United States Patent
Hofman et al.

(10) Patent No.: US 8,618,047 B2
(45) Date of Patent: Dec. 31, 2013

(54) LIQUID ENTERAL NUTRITIONAL COMPOSITION SUITABLE FOR TUBE FEEDING, MINIMIZING LOWER AND UPPER TRACT DIGESTIVE CONDITIONS

(75) Inventors: Zandrie Hofman, Bennekom (NL); Rogier Daniël van Anholt, Deventer (NL); Wynette Hermina Agnes Kiers, Zetten (NL); Marianne Klebach, Utrecht (NL); Marloes Heleen van Beusekom, The Hague (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 13/560,781

(22) Filed: Jul. 27, 2012

(65) Prior Publication Data

US 2013/0023468 A1     Jan. 24, 2013

Related U.S. Application Data

(63) Continuation of application No. PCT/NL2011/050060, filed on Jan. 31, 2011.

(30) Foreign Application Priority Data

Jan. 29, 2010   (WO) ................ PCT/NL2010/050041

(51) Int. Cl.
```
A23L 1/30      (2006.01)
A23L 1/29      (2006.01)
A23J 3/16      (2006.01)
A23L 1/305     (2006.01)
A61K 38/16     (2006.01)
```

(52) U.S. Cl.
USPC ................ 514/5.6; 514/5.5; 514/4.8; 514/5.7

(58) Field of Classification Search
CPC .......... A23L 1/30; A23L 1/29; A23L 1/3056; A61K 38/16; A23J 3/16
USPC ..................... 514/4.8, 5.5, 5.6, 5.7
See application file for complete search history.

(56) References Cited

U.S. PATENT DOCUMENTS

| | | | |
|---|---|---|---|
| 2010/0086668 A1 * | 4/2010 | Abrahamse et al. | 426/661 |
| 2012/0283180 A1 * | 11/2012 | Hofman et al. | 514/5.6 |
| 2012/0309831 A1 * | 12/2012 | Van Anholt et al. | 514/560 |

FOREIGN PATENT DOCUMENTS

| | | | |
|---|---|---|---|
| EP | 0626175 A2 * | 9/1993 | |
| EP | 0 626 175 A2 | 11/1994 | |
| EP | 0 626 176 A2 | 11/1994 | |
| EP | 1 972 345 A1 | 9/2008 | |
| EP | 1972345 A1 * | 9/2008 | |
| EP | 2 073 781 A2 | 7/2009 | |
| WO | WO 9319624 A1 * | 10/1993 | |
| WO | WO-2008/046871 A2 | 4/2008 | |

OTHER PUBLICATIONS

International Search Report for PCT/NL2011/050060—mailed Mar. 16, 2011.

* cited by examiner

*Primary Examiner* — Cecilia J Tsang
*Assistant Examiner* — Kristina M Hellman
(74) *Attorney, Agent, or Firm* — Gilberto M. Villacorta; Sunit Talapatra; Foley & Lardner LLP

(57) ABSTRACT

The invention is directed to liquid enteral nutritional compositions comprising a protein fraction comprising more than 25 weight % and up to 80 weight % of a vegetable protein comprising at least a source of pea protein, and a fat fraction comprising (a) 8 to 15 weight % of linoleic acid; (b) 3.0 to 6.0 weight % of a combination of alpha-linolenic acid, docosahexaenoic acid and eicosapentaenoic acid, wherein the amount of ALA is >2.5 weight % and the combined amount of DHA and EPA is ≤2.5 weight %; (c) 10 to 20 weight % of at least one medium-chain fatty acid; and (d) 35 to 79 weight % of at least one mono-unsaturated fatty acid. The compositions provide for a healthy and balanced diet, which is well-tolerated and minimises clinical complications that are frequently associated with the administration of enteral nutrition in patients using tube feeding, especially with respect to a reduced gastric emptying.

12 Claims, No Drawings

LIQUID ENTERAL NUTRITIONAL COMPOSITION SUITABLE FOR TUBE FEEDING, MINIMIZING LOWER AND UPPER TRACT DIGESTIVE CONDITIONS

CROSS REFERENCE TO RELATED APPLICATIONS

This application is a Continuation of International Application No. PCT/NL2011/050060, filed Jan. 31, 2011, which claims priority to International Application No. PCT/NL2010/050041, filed Jan. 29, 2010. The content of which is hereby incorporated by reference in its entirety.

FIELD OF THE INVENTION

The invention relates to a liquid enteral nutritional composition comprising a specifically designed pea-based protein fraction, a fat fraction, and optionally a dietary fibre fraction, (a) which meets all nutritional needs in accordance with the general recommendations for a healthy and balanced diet, (b) which is well-tolerated and minimises clinical complications that are frequently associated with the administration of enteral nutrition in patients using tube feeding, especially with respect to a reduced gastric emptying, and (c) which is suitable for tube feeding.

Clinical Problem

Due to a variety of reasons, such as diseases, medical conditions, malnutrition, medical disabilities, post-surgery, etc. patients may not be able to obtain the necessary nutrition by ingesting food through the mouth, e.g. orally, by eating or drinking. Specific indications include severe protein-energy malnutrition, coma, inability to take oral feedings due to head or neck trauma, Crohn's disease, neurological disorders resulting in dysphagia, cerebral vascular accidents, surgery, and critical illnesses (e.g., burns) causing metabolic stress. Therefore, it has been known to provide medical enteral nutrition by oral nutritional supplements or by tube feeding. Tube feeding is given to provide nutrition to patients which cannot obtain nutrition by swallowing, using a device such as a nasogastric feeding tube or a naso jejunal feeding tube, or by using a percutaneous endoscopic gastrostomy (PEG) or PEG-jejuno-feeding system.

In the context of this application, the state of being fed by nutritional supplements or by a feeding tube is called enteral feeding, comprising all of the abovementioned tube feeding modes, and the nutrition used in such feeding is called enteral nutrition. Use of such enteral nutrition may be temporary for the treatment of acute conditions, or lifelong in the case of chronic disabilities. Generally, said enteral nutrition is administered to patients in hospitals, in nursing homes and to subjects in the context of home care, where administration of enteral nutrition, in particular by tube feeding, is of a chronic nature (such as long-term enteral feeding).

Therefore, especially for subjects requiring tube nutrition for longer periods of time in combination with modern advances in medicine resulting in increased life expectancy and better disease treatment, it is important to provide an optimal product composition, (a) to meet all nutritional needs, especially with regard to the protein, fat and carbohydrate components over a longer period of time, and (b) to minimise clinical complications that are frequently associated with the administration of enteral nutrition in patients using tube feeding.

Such clinical complications are, for example, vomiting, nausea, reflux, diarrhoea, constipation, and retention. A distinction can be made between upper and lower digestive tract complications. Lower digestive tract complications typically are diarrhoea and constipation; upper digestive tract complications typically are a reduced gastric emptying, retention, reflux, vomiting, aspiration, and pneumonia. Moreover, a reduced gastric emptying is a risk factor for increased reflux, vomiting, and aspiration and therefore for the development of pneumonia.

Technical Problem

Furthermore, the liquid enteral nutritional composition according to the invention should be (c) suitable as a tube feed and easy to be administered by tube, i.e. it should have a low viscosity and a low density, it should be pH neutral, have a long shelf live, have a good shelf stability, not segregate, agglomerate or sedimentate. It should be suitable for heat treatments (such as sterilization and pasteurization) without a substantial change in structure, palatability (especially for oral nutritional compositions), viscosity, etc. The protein and fat fractions should be easily mixable with other components, such as a carbohydrate fraction, a digestible fibre fraction, and other components, e.g. to provide a complete liquid enteral nutritional composition.

BACKGROUND PRIOR ART

Up to know, little attention has been given to the development of liquid enteral nutritional compositions suitable for tube feeding which meet all of the above conditions (a), (b) and (c).

EP 1 972 345 A1 (Katry Inversiones) discloses a pea-based food product intended for enteral or oral nutrition containing a protein fraction with a specific amino acid profile, a lipid mixture, carbohydrates, soluble and insoluble fibre, vitamins and minerals, in particular a pea-based protein fraction consisting of 50 weight % caseinate, 25 weight % milk serum proteins and 25 weight % pea protein and a fat mixture containing specific fatty acid proportions. Although the nutritive qualities of the claimed food product are evaluated, no data are available on clinical complications when ingested by humans, in particular when used as a tube feed.

EP2073781 A2 (Nestec SA) discloses specific long term tube nutritional compositions for specific patient populations, such as elderly. Neither the nutritive qualities of the claimed food product are evaluated, nor data are available on clinical complications when ingested by humans, in particular when used as a tube feed.

Furthermore, it is known in literature that different proteins and fats can influence gastric emptying in a different way. For example, casein is coagulating in the stomach while whey proteins are not coagulating in the stomach. Hence, casein is regarded as a coagulation protein with slow gastric emptying properties and whey proteins are regarded as non-coagulating proteins with a much faster gastric emptying. It is unknown whether or not other proteins are coagulating in the stomach or whether or not they may influence gastric emptying.

BRIEF DESCRIPTION OF THE INVENTION

It is the aim of this invention to provide a liquid enteral nutritional composition, (a) which meets all nutritional needs, especially with regard to the protein and fat components, in accordance with the general recommendations for a healthy and balanced diet, (b) which is well-tolerated and minimises clinical complications that are frequently associated with the administration of enteral nutrition in patients using tube feeding, especially with respect to a reduced gastric emptying, and (c) which is suitable for tube feeding with regard to typical parameters such as stability, shelf live, viscosity, etc.

Surprisingly, the inventors found that said goal could be achieved by a liquid enteral nutritional composition as disclosed in any one of the appended claims, comprising an innovative and novel pea-based protein fraction comprising more than 25 weight % and up to 80 weight % of a vegetable protein comprising at least a source of pea protein, and an innovative and novel fat fraction comprising (a) 8 to 15 weight % of linoleic acid (LA); (b) 3.0 to 6.0 weight % of a combination consisting of the ω-3 poly-unsaturated fatty acids alpha-linolenic acid (ALA), docosahexaenoic acid (DHA) and eicosapentaenoic acid (EPA), wherein the amount of ALA >2.5 weight % and the combined amount of DHA and EPA ≤2.5 weight %; (c) 10 to 20 weight % of at least one medium-chain fatty acid (MCFA); and (d) 35 to 79 weight % of at least one mono-unsaturated fatty acid (MUFA).

The innovative and novel protein and fat fractions are each separately claimed in two copending applications and are believed to provide for the optimal nutritional need (condition (a)), whereas combined in the liquid enteral nutritional composition according to the invention, they minimise clinical complications, especially of the upper digestive tract (condition (b)).

In a further embodiment, to minimize lower digestive tract complications, the liquid enteral nutritional composition according to the invention further may comprise any dietary fibres, or any mixture of dietary fibres, in particular as disclosed in EP 0756828 B1. More in particular, the liquid enteral nutritional composition comprises 5 to 120 g/l of dietary fibre, wherein the dietary fibre fraction consists of 15 to 50 weight % of soluble non-starch polysaccharides, 15 to 45 weight % of insoluble non-starch polysaccharides, 8 to 70 weight % of non-digestible oligosaccharides comprising at least 8 weight %, on the basis of fibre, of hydrolysed inulin, and comprising resistant starch.

In a further embodiment, the liquid enteral nutritional composition according to the invention further comprises one or more of a carbohydrate fraction and micronutrients.

A lower incidence of clinical indications was observed for the composition according to the invention, compared to a composition according to the state of the art, in particular for clinical complications of the upper digestive tract (nausea, vomiting, use of antacids), but also for clinical complications of the lower digestive tract (diarrhoea, constipation), gastrointestinal-related adverse events, pneumonia-related adverse events and serious adverse events.

DETAILED DESCRIPTION OF THE INVENTION

Protein Fraction

According to one embodiment, the pea-based protein fraction comprises more than 25 weight % and up to 80 weight % of vegetable protein comprising at least a source of pea protein.

According to one embodiment, the pea-based protein fraction comprises at least 8 En %, preferably at least 10 En %, more preferably at least 15 En % of the total energy of the composition.

According to one embodiment, the liquid nutritional composition according to the invention preferably contains between 1 and 20 gram of proteins per 100 ml, more preferably between 2 and 15 grams per 100 ml, more preferably 2, 3, 4, 5, 6, 7, 8, 9, 10, 11, 12, 13, 14, or 15 grams of proteins per 100 ml of a liquid product or any integer and non-integer fraction in between.

In the context of this application, when referring to a "protein mixture", a "protein fraction", or a "protein composition" according to the invention, is meant a collection of proteins, proteinaceous matter, peptides and amino acids, free or in any bound form. Hence, the protein fraction of a nutritional composition is the sum of all proteins, proteinaceous matter, peptides and amino acids, free or in any bound form present in the nutritional composition. Furthermore, the wording "protein mixture" refers to a collection of proteins, proteinaceous matter, peptides and amino acids as such, in any form, as well as to a collection of proteins, proteinaceous matter, peptides and amino acids simultaneously present in a matrix, such as an aqueous matrix, such as a liquid enteral nutritional composition. In the latter case, the protein mixture may be referred to as a protein fraction of that matrix.

In the context of this application, the pea-based protein fraction essentially consists of vegetable and dairy proteinaceous matter, in particular proteins.

In the context of this application, the wording "vegetable" relates to protein from plant origin, such as, for instance originating from vegetables such as carrot, pea, chickpea, green pea, cowpea, field pea kidney bean, lupine, rice, soy, canola, hemp, zein, maize, corn, barley, flax, linseed, and wheat. Equivalent wording may be used, such as "vegetal", "leguminous" or "plant-derived".

In the context of this application, the wording "dairy" protein relates to milk-derived protein, i.e. to protein derived from animal milk, such as derived from species such as camel, cow, goat, horse, human, reindeer, sheet, water buffalo and yak.

In one embodiment, the pea-based protein fraction according to the invention comprises 30 to 50 weight %, more in particular 35 to 45 weight % of intact vegetable protein relative to the total protein in the protein fraction.

The pea-based protein fraction according to the invention may have any physical form, such as a powder or liquid form, and it may be a solution, suspension, dispersion or the like. Preferably, the pea-based protein fraction according to the invention is in liquid form. Preferably, the pea-based protein fraction is an aqueous protein fraction.

Pea Protein

In the past, pea protein alone is generally classed as quite a poor vegetable source of protein, having a Biological Value (BV) of about 49% when compared to e.g. whole egg (100%), cow's milk (91%), casein (77%), soy (74%) and wheat (54%) (see e.g. Renner, E. (1983) *Milk and dairy products in human nutrition*. Volkswirtschaftlicher Verlag, Munich, Germany) and having an amino acid score (AAS) which is below the one for whole egg (1), cow's milk (1), casein (1) and soy (0.91). The BV of a protein is the amount of nitrogen used for tissue formation divided by the amount absorbed from the food and is expressed as a percentage. The AAS is the ratio between the amount of the first limiting amino acid in the protein under study (mg/g) and the amount of that amino acid in a reference protein (mg/g), optionally multiplied by the true digestibility (Protein Digestibility Corrected-AAS, PDCAA). According to the WHO (2007) recommendations on protein quality as the reference, pea has an amino acid score of below 1.0 due to the relatively low methionine content.

In all powders, pea protein tastes quite bad (even in intact form) and it doesn't mix too well, leaving a kind of grainy texture to the protein. However, the inventors have found that intact pea protein could be combined with one or more second proteins, preferably an intact vegetable protein, such as whey protein in a concentration over and above 25 weight %, such that a good overall mix of amino acids could be obtained and an almost time-released composition. The whey proteins enter the blood stream very fast, while the pea proteins are absorbed much slower.

Pea protein is relatively cheap (on the average, pea protein may cost about half the price of caseinates) and is added to the mixture to increase the protein content while keeping costs quite low. Pea protein is generally tolerated well by most people, it is lactose-free and is not a common allergen. Pea protein is quite high in cysteine content and can therefore compensate the inadequate amount of cysteine in casein proteins. Furthermore, pea protein is quite high in arginine compared to casein, soy or whey protein which is required for muscle metabolism and which facilitates the intake of body mass while reducing body fat; and it is quite high in lysine, when compared to the vegetable proteins, which is needed to build protein muscle and assist in the maintenance of lean body mass. Intact pea was found to be substantially a non-coagulating protein in the stomach of a human person, which means that intact pea protein do not coagulate in the stomach of a human person under normal digestive conditions. Coagulation of proteins in the stomach is hypothesized to delay gastric emptying, This will result in upper gastrointestinal complications such as, e.g. intestinal discomfort, aspiration pneumonia, high gastric residual volume (GRV), vomiting, nausea, bloating, and delayed gastric emptying, especially in vulnerable persons, such as hospitalized patients. Hence, the finding that intact pea protein is a non-coagulating protein may provide a source of easily-digestible vegetable proteins.

Several pea sources are readily available to the skilled person, for example, from ROQUETTE™ (Lestrem, France) which markets a pea isolate obtained from the yellow pea (*Pisum sativum*), and from COSUCRA™ Groupe Warcoing (Warcoing, Belgium).

According to one embodiment, the pea protein is substantially in intact form or non-hydrolysed. In the context of this application, a "non-hydrolysed" protein is equivalent to an "intact" protein, meaning that the protein has not been subjected to an hydrolysis process. However, minor amounts of hydrolysed proteins may be present in the source of non-hydrolysed proteins, or may be added to the formulation, such as additional amino acids, such as, for example leucine, iso-leucine, glutamine, arginine, or dipeptides and the like. In one embodiment of the present invention, the composition may comprise a free amino acid, or a mixture of free amino acids, up to 5 gram/100 ml, more preferably less than 2 gram/100 ml, more preferably less than 1 gram/100 ml, most preferably less than 0.5 gram/100 ml. According to another embodiment, intact protein may only posses a degree of hydrolysis (DH) of 10% of lower, preferably 9, 8, 7, 6, 5, 4, 3, 2, 1% or lower.

In this context, "minor" should be understood as an amount of about 10 weight % or less. The term "about" should be interpreted as a deviation of plus or minus 10% of the given value.

According to another embodiment, the pea-based protein fraction according to the invention comprises 5 to 60 weight %, in particular 10 to 30 weight %, more in particular 15 to 25 weight % of pea protein, relative to the total protein in the protein fraction.

Second Vegetable Protein

The pea-based protein fraction according to the invention may further comprise a second vegetable protein, other than pea protein. Preferably, the second vegetable protein is selected from a group of soy, rice, and wheat protein. Preferably, the second vegetable protein is soy protein.

In one embodiment, the second vegetable protein is substantially in intact form.

According to one embodiment of the invention, the second intact vegetable protein is substantially a non-coagulating protein in the stomach of a human person.

Soy Protein

It was found that intact soy is substantially a non-coagulating protein in the stomach of a human person, which means that intact soy protein do not coagulate in the stomach of a human person under normal digestive conditions. Coagulation of proteins in the stomach is hypothesized to delay gastric emptying, This will result in upper gastrointestinal complications such as, e.g. intestinal discomfort, aspiration pneumonia, high gastric residual volume (GRV), vomiting, nausea, bloating, and delayed gastric emptying, especially in vulnerable persons, such as hospitalized patients. Hence, the finding that intact soy protein is a non-coagulating protein may provide a source of easily-digestible vegetable proteins.

Soy protein has been used since 1959 as an ingredient for its functional properties in a variety of foods such as salad dressings, soups, vegetarian foods and meat imitations. Its functional properties are emulsification and texturizing. Recently, the popularity of soy protein is increasing, mainly because of its health benefits. It has been proven that soy protein can help to prevent cardiovascular problems and many countries allow health claims for food, which are rich in soy protein. Furthermore, health claims have been made for improving heart health (cholesterol reduction), improving bone health (increased bone density), menopausal symptom relief (reduced hot flashes), performance nutrition (faster muscle recovery) and weight management (satisfying hunger). Soy protein is a vegetable protein that contains the essential amino acids in a relatively high proportion for human health. Soy protein is categorized as a high-quality, complete protein although the methionine level is slightly below the WHO 2007 recommendation for methionine content.

Soy proteins can be divided into different categories according to their production method. Soy protein isolate (SPI) is the most refined form of soy protein and is mainly used in meat products to improve texture and eating quality. Soy protein isolate contains about 90 percent protein. Soy protein concentrate (SPC) is basically soybean without the water soluble carbohydrates. It contains about 70 percent of protein. Textured soy protein (TSP) is made from soy protein concentrate by giving it some texture. TSP is available as dry flakes or chunks. It will keep its structure when hydrated. Hydrated textured soy protein chunks have a texture similar to ground beef. It can be used as a meat replacement or can be added to meat. Textured soy protein contains about 70 percent protein.

Several soy sources are readily available to the skilled person, for example, from The SOLAE™ Company (St. Louis, Mo., USA).

Dairy Proteins

According to one embodiment, the pea-based protein fraction according to the invention further comprises a dairy protein. Preferably, the dairy protein is selected from the group of casein and whey protein.

Preferably, the pea-based protein fraction according to the invention comprises 20 to 75 weight %, in particular 50 to 70 weight %, more in particular 55 to 65 weight % of at least one or more dairy proteins, relative to the total protein in the protein fraction.

Preferably, the dairy protein is included in substantially intact (unhydrolyzed) form, in order to have a palatable product. Such high molecular weight proteins increase the viscosity of the heat-treated liquid product, compared to the hydrolyzed forms. The present inventors were able to make a product with good palatability and low viscosity, by applying the measures according the invention. Furthermore, the dairy proteins compensate for the relatively low methionine content of the vegetable proteins in order to have an amino acid score above 1.0 for the total protein fraction.

Whey Proteins

One of the most superior classes of food protein is whey protein. It is known for its excellent amino acid profile, for its ability to increase the protein synthesis in a mammal (due to a higher leucine content), for its improved tolerance and increased gastric emptying, and for its interesting bioactive proteins with immune enhancing properties (lactoglobulins, immunoglobulins, lysozyme, glutamine, cysteine and lactoferrins). Nutritionally speaking, whey protein is known as a naturally complete protein because it contains all of the essential amino acids required in the daily diet. It is also one of the richest sources of branched chain amino acids (BCAAs, in particular leucine) which play an important role in muscle protein synthesis. Moreover, some of the individual components of whey protein have been shown to prevent viral and bacterial infection and modulate immunity in animals. Whey protein is the preferred choice of proteins to treat persons suffering from sarcopenia, but is also suitable for healthy persons, such as sportsmen and active elderly. Furthermore, whey is also a non-coagulating protein, as stated above.

As a source of whey protein to be used in the present invention, any commercially available whey protein source may be used, i.e. whey obtained by any process for the preparation of whey known in the art, as well as whey protein fractions prepared thereof, or the proteins that constitute the bulk of the whey proteins being β-lactoglobulin, α-lactalbumin and serum albumin, such as liquid whey, or whey in powder form, such as whey protein isolate (WPI) or whey protein concentrate (WPC). Whey protein concentrate is rich in whey proteins, but also contains other components such as fat, lactose and glycomacroprotein (GMP), a casein-related non-globular protein. Typically, whey protein concentrate is produced by membrane filtration. On the other hand, whey protein isolate consists primarily of whey proteins with minimal amounts of fat and lactose. Whey protein isolate usually requires a more rigorous separation process such as a combination of microfiltration and ultra-filtration or ion exchange chromatography. It is generally understood that a whey protein isolate refers to a mixture in which at least 90 weight % of the solids are whey proteins. A whey protein concentrate is understood as having a percentage of whey proteins between the initial amount in the by-product (about 12 weight %) and a whey protein isolate. In particular, sweet whey, obtained as a by-product in the manufacturing of cheese, acid whey, obtained as a by-product in the manufacturing of acid casein, native whey, obtained by milk microfiltration or rennet whey, obtained as a by-product in the manufacturing of rennet casein, may be used alone or in combination as source of globular whey proteins.

Furthermore, whey proteins may originate from all kinds of mammalian animal species, such as, for instance cows, sheep, goats, horses, buffalo's, and camels. Preferably, the whey protein is of bovine origin.

Preferably, the whey protein source is available as a powder, preferably the whey protein source is a WPC or WPI.

Casein/Caseinate

Casein is one of the two types of protein found in milk, the other being whey.

Casein separates from milk when milk is curdled, a process commonly carried out in the manufacturing of cheese, and is commonly called caseinate, having lost its typical micellar structure. Casein tends to form a gel in the stomach, which slows the digestion. This makes casein an ideal protein source to release protein into the bloodstream over a period of time, e.g. during sleep. Casein has also a high glutamine content, a conditionally essential amino acid, necessary for repair of muscle tissue after strenuous exercise and important for gut and immune function. Casein has a relatively low cysteine content which can be compensated by adding other proteins like vegetable proteins. Cysteine is important for the endogenous synthesis of glutathione and therefore plays an important role to protect damage from free radicals.

Like many other nutritional compounds, casein is typically bound to a metal ion since the molecule is more stable this way. Specifically, casein is most commonly bound to calcium ($Ca^{2+}$) and sodium ($Na^+$) since all of these ions are found naturally in milk, or even potassium ($K^+$) or magnesium ($Mg^{2+}$), and tend to stick to the casein during the extraction process. Nutritionally, these compounds are basically interchangeable, as all forms of casein are effective protein sources. Micellar casein refers to casein in the form of native micelles. It is a high quality milk protein and naturally occurring in milk in a concentration of about 2.6 g/100 ml (Dairy Science and Technology, Walstra et al., CRC Press, 2006). It is concentrated by a process that does not, or does not substantially denature the casein proteins and it is marketed as Micellar Casein Isolate (MCI). Fresh skim milk is subjected to a microfiltration process, in much the same process used to concentrate whey protein, to produce a pure, substantially undenaturated milk protein with its native structure. The resulting material contains between 90% and 95%, preferably more than 95% by weight of micellar casein, the rest mainly being whey protein and other non-protein nitrogen and other constituents, such as lactose and inorganic salts, in particular calcium phosphate.

Within the context of this invention, it is understood that micellar casein may also be provided by other milk protein sources, such as, for instance, sources with essentially preserve the natural 80:20 ratio of casein to whey, such as Milk Protein Concentrate (MPC), which is a powder product usually prepared by ultrafiltration with an average protein content of about 80 weight %, Milk Protein Isolate (MPI), a powder product usually prepared by precipitation with an average protein content of more than 85 weight %, and skimmed concentrated milk.

Within the context of this invention, with the term "casein" both caseinate and micellar casein is indicated.

In one embodiment, the casein is caseinate, preferably Na-caseinate or Ca-caseinate. Preferably, the caseinate is Ca-caseinate.

According to one embodiment, the protein mixture further comprises a dairy protein selected from the group of Na-caseinate, Ca-caseinate, micellar casein and whey protein.

Preferred Protein Fraction

According to a preferred embodiment, the pea-based protein fraction according to the invention comprises casein, whey protein, soy protein and pea protein, preferably comprising intact soy protein and intact pea protein. Preferably, all proteins are in substantially intact form.

According to a preferred embodiment, the pea-based protein fraction according to the invention consists 20 to 40 weight % of casein, 20 to 40 weight % of whey protein, 13 to 25 weight % of soy protein, and 13 to 25 weight % of pea protein, relative to the total protein in the protein fraction, wherein the sum of said proteins equals 100 weight %. The aforementioned pea-based protein fraction has an excellent amino acid profile.

Amino Acid Profile of the Pea-Based Protein Fraction

The pea-based protein fraction according to the invention at least meets and preferably exceeds the WHO amino acid profile recommendations for complete nutrition.

In one embodiment, the pea-based protein fraction according to the invention has the following amino acid profile in gram per 100 gram total protein in the protein fraction:

Cysteine: at least 1.1 g/100 g
Phenylalanine: at least 4.0 g/100 g
Tyrosine: at least 3.7 g/100 g.

In another embodiment, the pea-based protein fraction according to the invention has the essential amino acid profile range as given in Table 1 in gram per 100 gram total protein in the protein fraction. In the right column, the minimum amount according to WHO 2007 Guidelines is given.

TABLE 1

| Amino acid (essential and semi-essential) | Range according to invention (g/100 g) | Minimum amount (WHO, 2007)[a] (g/100 g) |
| --- | --- | --- |
| Histidine | 2.0 to 2.6 | 1.5 |
| Isoleucine | 5.2 to 6.4 | 3.0 |
| Leucine | 9.0 to 11.0 | 5.9 |
| Lysine | 7.5 to 9.0 | 4.5 |
| Methionine | 1.7 to 2.3 | 1.6 |
| Cysteine | 1.1 to 1.7 | 0.6 |
| Threonine | 4.9 to 6.2 | 2.3 |
| Tryptophan | 1.2 to 1.6 | 0.6 |
| Valine | 5.5 to 6.9 | 3.9 |
| Phenylalanine | 4.2 to 5.2 | Phe + Tyr = 3.0 |
| Tyrosine | 3.7 to 4.7 | |

[a] based on mean nitrogen requirement of 105 mg nitrogen/kg per day (0.66 g protein/kg body weight per day).

In a further embodiment, the pea-based protein fraction according to the invention has the amino acid profile range as given in Table 2 in gram per 100 gram total protein in the protein fraction, or the specific amino acid profile as given in the right column of Table 2.

TABLE 2

| Amino acid (essential, semi-essential and non-essential) | Range according to invention (g/100 g) | Specific amino acid profile (g/100 g) |
| --- | --- | --- |
| Histidine | 2.0 to 2.6 | 2.3 |
| Isoleucine | 5.2 to 6.4 | 5.8 |
| Leucine | 9.0 to 11.0 | 9.8 |
| Lysine | 7.5 to 9.0 | 8.3 |
| Methionine | 1.7 to 2.3 | 2.0 |
| Cysteine | 1.1 to 1.7 | 1.4 |
| Threonine | 4.9 to 6.2 | 5.6 |
| Tryptophan | 1.2 to 1.6 | 1.4 |
| Valine | 5.5 to 6.9 | 6.2 |
| Phenylalanine | 4.2 to 5.2 | 4.8 |
| Tyrosine | 3.7 to 4.7 | 4.1 |
| Alanine | 4.0 to 5.1 | 4.6 |
| Arginine | 4.5 to 5.7 | 5.2 |
| Aspartic Acid/Asparagine | 9.5 to 11.7 | 10.7 |
| Glutamic acid/Glutamine | 18.0 to 22.8 | 20.2 |
| Glycine | 2.6 to 3.2 | 2.9 |
| Proline | 5.8 to 7.3 | 6.5 |
| Serine | 5.3 to 6.5 | 5.9 |

Preparation of the Protein Fraction

The pea-based protein fraction according to the invention is prepared by mixing the pea protein and one or more individual proteins in powder form with water, for instance by dumping the individual powder proteins out of Totebin® containers into water, optionally comprising soluble carbohydrates, such as maltodextrins, and mixing the resulting solution. The temperature of the water, optionally comprising carbohydrates, is preferably between about 20 and about 60 degrees Celsius. For instance, when a maltodextrine syrup is used, the temperature is about 60 degrees Celsius, being the temperature of the syrup. The carbohydrates may also be added at a later stage. In principle, the protein mixture has now been prepared, but further ingredients may be added, such as minerals, fibres, fat, etc. Pasteurization of the protein mixture may be conducted without substantially raising its viscosity. For instance, pasteurization may be done for 30 seconds at 85° C., followed by a homogenization at 550 bar pressure, followed by cooling down the solution to 4 to 20° C. The pH of the resulting solution may be adjusted, for instance to pH=8, and the resulting solution may be further sterilized in an autoclave. The time/temp profile is dependent on the type of packaging, the resulting product and the F0-value, for instance for a bottled product the time/temperature profile is 121.5 to 122.5° C. during 16 minutes.

Fat Fraction

To arrive at the fat fraction of the invention, the inventors have first established that there are no recommendations for a fat fraction for patients in need of enteral medical nutrition. To overcome this problem, the inventors have collected a substantial number of recommendations and/or guidelines for a healthy and balanced dietary fat intake of national and international organizations. From this, the inventors defined a range which is defined by the lowest maximum and the highest minimum of those recommendations. Subsequently, the recommendations (in En %) were redefined in terms of weight % and a suitable fat source was researched, however, not a single fat source was able to fulfil the recommendations. Hence, a composition of fat sources was designed to yield the desired fat fraction.

After due consideration, the inventors have found that said fat fraction should comprise at least specific amounts of linoleic acid (LA, 18:2n-6), alpha-linolenic acid (ALA, 18:3n-3), docosahexaenoic acid (DHA, 22:6n-3), eicosapentaenoic acid (EPA, 20:5n-3), at least one medium chain fatty acid (MCFA, e.g. 8:0 and/or 10:0), and at least one monounsaturated fatty acid (MUFA, e.g. 16:1, 18:1, 20:1, 22:1 and/or 24:1). More in particular, the fat fraction contains lower amounts of LA than found in the prior art, in particular in commercial products available from, for example, ABBOTT™, FRESENIUS™, NESTLÉ™, AND NUTRICIA™.

Surprisingly, said fat fraction could be designed based on common fat sources, could easily be manufactured and could be used for the manufacture of the liquid enteral nutritional composition according to the invention.

According to one embodiment, the liquid enteral nutritional composition according to the invention comprises a fat fraction which comprises 8 to 15 weight %, preferably 12.5 to 14.5 weight %, most preferably 13.5 to 13.9 weight % of linoleic acid (LA, 18:2n-6);

3.0 to 6.0 weight %, preferably 4.0 to 5.0 weight %, most preferably 4.3 to 4.7 weight % of a combination consisting of the ω-3 poly-unsaturated fatty acids alpha-linolenic acid (ALA, 18:3n-3), docosahexaenoic acid (DHA, 22:6n-3) and eicosapentaenoic acid (EPA, 20:5n-3), wherein the amount of ALA >2.5 weight %, more preferably >2.7 weight %, or preferably ranges between 2.5 and 4.0 weight %, and the combined amount of DHA and EPA ≤2.5 weight %, preferably ≤1.0 weight %;

10 to 20 weight %, preferably 14 to 18 weight %, most preferably 15.7 to 16.2 weight % of at least one medium-chain fatty acid (MCFA, e.g. 8:0 and/or 10:0); and 35 to 79 weight %, preferably 40 to 70 weight %, most preferably 50 to 60 weight % of at least one mono-unsaturated fatty acid (MUFA, e.g. 16:1, 18:1, 20:1, 22:1 and/or 24:1).

wherein all relative amounts are calculated based on the total amount of fatty acids in the fat fraction. The relative amounts do not need to add up to 100 weight % as the fat fraction according to the invention may also include other types of fat.

Alternatively, the present invention relates to a liquid enteral nutritional composition wherein the fat fraction comprises between 30 and 50 En %, preferably between 30 and 40 En % of the total energy of the composition.

According to one embodiment, the liquid nutritional composition according to the invention preferably contains between 1 and 20 gram of fat per 100 ml, more preferably between 2 and 15 grams per 100 ml, more preferably 2, 3, 4, 5, 6, 7, 8, 9, 10, 11, 12, 13, 14, or 15 grams of fat per 100 ml of a liquid product or any integer and non-integer fraction in between.

In the context of this application, the % of total energy is also abbreviated as En %; En % is thus short for energy percentage and represents the relative amount that a constituent contributes to the total caloric value of the composition.

In the context of this application, the term "at least" also includes the starting point of the open range. For example, an amount of "at least 95 weight %" means any amount equal to 95 weight % or above.

In the context of this application, the term "about" defines a range of plus or minus 10% of the cited value. For example, an amount of "about 20 weight %" means any amount within the range of 18 to 22 weight %.

Fatty Acid Metabolism

Strictly speaking, the polyunsaturated fatty acids (PUFAs) linoleic acid (18:2n-6, abbreviated as LA, an omega-6 fatty acid) and α-linolenic acid (18:3n-3, abbreviated as ALA, an omega-3 fatty acid) are the only essential fatty acids for humans; all other physiologically and structurally important fatty acids can be derived from these two fatty acids. Nevertheless, the conversion of LA into the longer-chain fatty acid arachidonic acid (20:4n-6, ARA) and the conversion of ALA into eicosapentaenoic acid (20:5n-3, EPA) and docosahexaenoic acid (22:6n-3, DHA) by elongase and desaturase enzymes is not very efficient in humans. Estimates of conversion of LA into ARA and of ALA into EPA vary, but rarely exceed 10%. Moreover, the conversion of ALA into DHA is estimated to be even lower, with estimates varying from 4% to only 0.2% (Gerster 1998; Burdge et al. 2002; Goyens et al. 2006). These fatty acids (ARA, EPA, DHA) not only have important structural roles, but they are also converted into eicosanoids and resolvins with a range of physiological and immunological functions (Tapiero et al. 2002; Calder 2006; Serhan 2006). ARA, EPA, and DHA are called long-chain PUFAs (LCPUFA, PUFAs with a carbon chain length of more than 18) or LCPs, with ARA belonging to the omega-6 LCPUFAs and EPA and DHA belonging to the omega-3 LCPUFAs.

The composition of a diet largely determines the incorporation of these fatty acids into various cells and tissues in a complex way. Most importantly, the fatty acids, either derived from the diet or synthesised from precursors, compete on various levels for the same enzymes that determine the incorporation into tissues and/or conversion into biologically active metabolites: for enzymes that determine (1) incorporation into phospholipids and tissues, (2) the release from membranes and other stores, (3) the conversion into other fatty acids, and (4) the conversion into various metabolites (eicosanoids, resolvins). These eicosanoids and resolvins are involved in a wide variety of physiological and immunological processes, regulate the release of a range of hormones and have an effect on nervous system function. Due to the competition of fatty acids for the converting enzymes, a relative excess in LA consumption will promote the formation of ARA at the expense of EPA and DHA. Similarly, a relative excess in ALA leads to a higher production of EPA and DHA over ARA. Consequently, this will result either in a shift toward ARA-derived metabolites, or to EPA and DHA-derived metabolites. In this way, both the absolute amounts and the ratios between the different fatty acids in the diet affect the structural and regulatory roles of the fatty acids and their metabolites.

Table 3 gives a Schematic representation of the metabolism of fatty acids in humans that starts with the two essential fatty acids linoleic acid and α-linolenic acid from dietary (plant) sources. From these fatty acids all other important fatty acids can (theoretically) be derived by enzymatic conversion: desaturation enzymes (Δ5, Δ6) insert new double bounds between carbon atoms and the enzyme elongase adds carbon atoms to the carbon chain.

Table 3. Overview of the metabolism of the various fatty acids
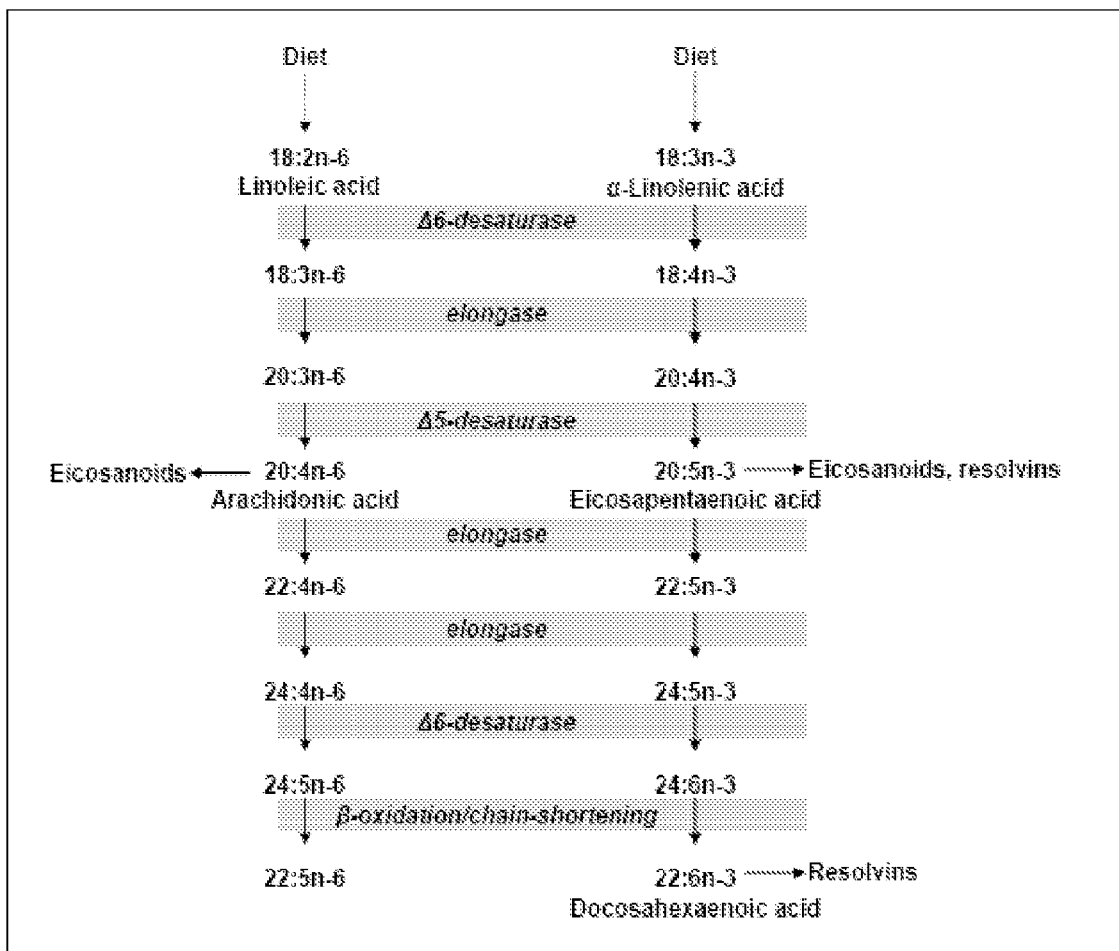

Overview of the Most Recent Recommendations

Several organizations have published guidelines for the composition of enteral nutrition, addressing the specific dietary needs of particular patient groups. For instance, ESPEN guidelines have been published for a number of patient populations (i.e. Cardiology and Pulmonology; Gastroenterology; Geriatrics; Hepatology; Wasting in HIV; Intensive care; Non-surgical oncology; Renal failure; Surgery and transplantation). However, none of these guidelines specifically address the optimal dietary composition for general enteral nutrition, nor are detailed recommendations for the fat composition included. On the other hand, recommendations for a healthy and balanced diet aimed at the general public are becoming increasingly more detailed as the insight in the role of nutrition in health and particularly prevention of diseases is progressing.

The availability and accessibility combined with the public awareness of healthy nutrition signifies the suitability of these dietary recommendations as a starting point when considering the fat composition of advanced medical nutrition products. Hence, it seems imperative that patients receiving general medical nutrition should benefit from the same dietary compositions that are considered advantageous for the general population. In order to determine the optimal levels of specific (groups of) fatty acids, a detailed comparison was made of the recommendations for a healthy and balanced dietary fat intake of the national and international organizations, which included, among others, the organizations listed below. The list shown is not intended to be complete, but it reflects the range of recommendations that apply to the "Western-type" diet:

Health Council of the Netherlands (Netherlands)
British Nutrition Foundation (U.K.)
Scientific Advisory Committee on Nutrition (U.K.)
Deutsche Gesellschaft für Ernährung (Germany)
Superior Health Council of Belgium (Belgium)
Agence Française de Sécurité Sanitaire des Aliments (AFSSA) & Centre National d'Études et de Recommandations sur la Nutrition et l'Alimentation (CNERNA)—Centre National de la Recherche Scientifique (CNRS) (France)
Società Italiana di Nutrizione Umana (Italy)
American Heart Association Nutrition Committee (U.S.A.)
Food and Agriculture Organization & World Health Organization (FAO/WHO)
International Society for the Study of Fatty Acids and Lipids (ISSFAL).

The view on a healthy fat intake has changed over the past decades, from a reduction of the overall fat intake to more emphasis on the distinction of different types of fat and the acknowledgement of so-called "healthy fats". Scientific insights on what should be considered optimal levels can differ between countries, resulting in a variety of recommendations. Nevertheless, several universal recommendations can be identified:

1. Reduce the total energy intake (in part) by a reduction of the fat intake;
2. Reduce the intake of trans fats (mainly derived from processed foods);
3. Reduce the intake of saturated fats;
4. Reduce the consumption of omega-6 fatty acids, in particular linoleic acid (LA, 18:3n-6);
5. Increase the consumption of long-chain omega-3 fatty acids EPA (20:5n-3) and DHA (22:6n-3), e.g. by increasing the consumption of (fatty) fish to at least 1-2 times per week.

In Table 4 the inventors combined recommendations into the range of what is considered a healthy and balanced intake for fatty acids: while none of the organisations provides recommendations/guidelines for all the aspects of an optimal fat intake, the combination of all recommendations/guidelines resulted in the most balanced composition that will comply with all recommendations/guidelines mentioned.

These recommendations are intended for the general (healthy) population with the primary goal to prevent illness and reduce mortality related to dietary practice, for example cardiovascular diseases. Although the fat compositions of current prior art sip and tube feeds correspond for the most part with the recommendations for a healthy and balanced fat intake, several differences can be identified, in general attributed to the incorporation of DHA and EPA, which is generally lacking in prior art products for enteral nutrition, and the LA-content, which is systematically too high in prior art products for enteral nutrition.

TABLE 4

The combined national and international recommendations from 13 national and international organizations for the intake of different types of fat. Recommendation values are expressed as percentages of the daily caloric food intake; daily intake calculated for 2 caloric diets, when these products are consumed as a full dietary replacement (complete nutrition).

|  | Highest minimum-Lowest maximum | Daily intake (g) with a 1500 kcal/day diet | Daily intake (g) with a 2000 kcal/day diet |
| --- | --- | --- | --- |
| Total fat | 15-35 En % | 25.0-58.3 g | 33.3-77.8 g |
| Saturated fat | Maximum 10 En % | Maximum 16.7 g | Maximum 22.2 g |
| Unsaturated fat | 15.3-33 En % | 25.5-55 g | 34.0-73.3 g |
| MUFA | 10-30 En % | 16.7-50.0 g | 22.2-66.7 g |
| PUFA | 5.3-12 En % | 8.8-20.0 g | 11.8-26.7 g |
| LA | Adequate 4 En % | Adequate 6.7 g | Adequate 8.9 g |
| ALA | Minimum 1 En % | Minimum 1.7 g | Minimum 2.2 g |
| LA/ALA | 2.9:1-4.3:1 | 2.9:1-4.3:1 | 2.9:1-4.3:1 |
| EPA + DHA | Minimum 0.27 En % | Minimum 450 mg | Minimum 600 mg |
|  | Minimum 500 mg/day | Minimum 500 mg | Minimum 500 mg |
| Total ω-6 | 4-8 En % | 6.7-13.3 g | 8.9-17.8 g |
| Total ω-3 | 1.3-2 En % | 2.2-3.3 g | 2.9-4.4 g |
| ω-6/ω-3 | 2.1:1-6.2:1 | 2.1:1-6.2:1 | 2.1:1-6.2:1 |

Implementation of the Recommendations

The inventors have now found that a fat fraction could be designed, taking into account the recommendations for a healthy and balanced fat intake, suitable for enteral nutrition. After due consideration, the following fat composition is proposed, which will be discussed in more detail in the next sections, and which takes into account:
1. Inclusion of a source of EPA and/or DHA: almost all organizations recommend a minimum intake of (fatty) fish of 1-2 times/week, which corresponds to a minimum daily intake of about 500 mg EPA+DHA.
2. Selection of the appropriate fat sources with a low LA content: several organizations recommend a reduction of the intake of LA to a minimum intake of 1 to 4 En % for adults.
3. Inclusion of medium-chain fatty acids (MCFA): adding a source of MCFAs provides an easy and relatively cheap way to reduce the LA content (see point 2 above). In order to reduce the LA content to 4 En %, an equivalent amount of 4 En % of MCFAs might be required (10-20% of the fat composition).
4. Inclusion of a source rich in a mono-unsaturated fatty acid (MUFA), for example, oleic acid (18:1n-9): several organizations recommend minimum or adequate intakes of MUFAs between 10 and 30 En %. Inclusion of sufficient amounts of MUFAs is an excellent way to limit the total saturated fatty acid amount, as well as replace the omega-6 PUFAs mentioned above.

In the framework of this application, the wording "balanced", "better balanced" and the like is used to indicate that the fat composition according to the invention is a better solution to the recommendations for a healthy and balanced fat intake than the existing, commercially available fat compositions.

1. Inclusion of a Source of EPA and/or DHA

Increasing the consumption of fish oil, high in the omega-3 fatty acids EPA and DHA, has an effect on a range of physiological and immunological processes, including membrane fluidity and functioning and signal transduction pathways. Most importantly, increasing the intake of EPA and DHA reduces the production of pro-inflammatory mediators such as cytokines, interleukins and tumour necrosis factor (TNF). This is achieved by (1) competition with the omega-6 arachidonic acid (20:4n-6, ARA) for the incorporation into membrane phospholipids, which lowers the ARA content of the cell membranes and hence its availability for eicosanoid synthesis, and (2) by competition for the same enzymes that convert ARA into pro-inflammatory eicosanoids (Calder 2006; Sijben et al. 2007).

Multiple (mechanistic) studies have confirmed that consumption of sufficient fish has the following beneficial effects:
reduction of serum inflammatory markers (e.g. Zampelas et al. 2005)
decrease in overall heart rate (e.g. Mozaffarian et al. 2005)
reduction of blood pressure (e.g. Theobald et al. 2007)
reduction of fasting and postprandial plasma triglycerides (e.g. Schwellenbach et al. 2006)
protection against heart arrhythmias, most likely by modulation of myocardial sodium and calcium ion channels (e.g. Chrysohoou et al. 2007).

A large number of interventions with elevated intakes of n-3 PUFA have been published with the objective to reduce symptoms of (and sometimes to treat) diseases related to chronic inflammation, including rheumatoid arthritis, asthma, cancer-associated cachexia, and inflammatory bowel disease. Other diseases that have been found to be influenced by consumption of fish oil fatty acids are, among others, cardiovascular diseases (CVD), macular degeneration, osteoporosis, depression, schizophrenia, Attention Deficit/Hyperactivity Disorder (ADHD), eating disorders, cancer, burns, and skin disorders (Calder 2006).

The composition and purity of the available fish oils vary considerably. Not only are these oils different in the total amount of EPA and DHA, but also the ratio of EPA to DHA is subject to variation (see Table 5). EPA and DHA have different functions in the human body; beneficial effects of EPA are principally contributed to the competitive inhibition of eicosanoid synthesis from ARA, attributes of DHA are often linked to membrane functioning. Despite these differences in functionality, many intervention studies provide very little information on the exact intake of these fatty acids, not in the least because these levels can be difficult to determine in the diet.

TABLE 5

Approximate fatty acid compositions (in grams per 100 gram) g) of several commonly used fish oils. Source: "The Lipid Handbook, third edition. 2007. F. D. Gunstone, J. L. Hardwood, A. J. Dijkstra (Eds.). CRC Press, USA.

|  | Anchovy | Sardine | Tuna |
| --- | --- | --- | --- |
| Saturated |  |  |  |
| 14:0 | 9 | 8 | 3 |
| 16:0 | 17 | 18 | 22 |
| Mono-unsaturated |  |  |  |
| 16:1 | 13 | 10 | 3 |
| 18:1 | 10 | 13 | 21 |
| Poly-unsaturated n − 3 |  |  |  |
| 20:5n − 3 (EPA) | 22 | 16 | 6 |
| 22:6n − 3 (DHA) | 9 | 9 | 22 |

The most commonly used fish species, i.e. anchovy and sardine, are characterised by a relative excess of EPA over DHA, while in contrast tuna oil is relatively rich in DHA (Table 5). Hence the ratio of EPA vs. DHA depends on the species that is used and the production process largely determines the quantity of these fatty acids. Apart from fish oil, which contains most of the EPA and DHA in the form of triglycerides, EPA and DHA can also be provided as purified ethyl-esters. For example, on e study showed that moderate supplementation with DHA (0.7 g DHA/day, from a purified algal source) lowered diastolic blood pressure within 3 months and this effect was more pronounced than obtained by higher doses of EPA and DHA combined in other studies (Theobald et al. 2007). Similarly, supplementation with 1 g/day of DHA was equally effective as 1.25 g EPA+DHA in reducing plasma triglycerides in male elderly after 8 weeks (Davidson et al. 1997). Omega-3 LCPUFAs from ethyl esters and triglycerides are equally well incorporated into plasma lipids, despite any possible differences in the initial timing of absorption (Luley et al. 1990; Hansen et al. 1993).

Dietary LCPUFAs can also be administered in the form of phospholipids, for example derived from eggs. While some studies reported a superior intestinal absorption of omega-3 LCPUFAs from phospholipids compared to triglycerides (Carnielli et al. 1998), others reported similar appearances of LCPUFAs in the plasma lipid fraction and virtually equal rates of incorporation of ARA and DHA in red blood cells from either phospholipids or triglycerides in infants (Sala-Vila et al. 2004; Sala-Vila et al. 2006).

As explained above, dietary α-linolenic acid (ALA) can be converted into long-chain omega-3 fatty acids EPA and DHA via enzymatic conversion. The possibility arises that by increasing the consumption of ALA, the tissue levels of EPA and DHA may be elevated. Rich sources of ALA are plant oils such as linseed oil (about 60% ALA), perilla oil (about 50% ALA), and canola oil (about 10%). However, the conversion of ALA into EPA (less than 10% of dietary ALA) and into DHA (less than 4% of dietary ALA) in adults is not very efficient and is even further reduced by 40-50% with a background diet high in omega-6 PUFAs (Gerster 1998; Williams et al. 2006). This suggests that high intakes of ALA will be required to reach the equivalent of the recommended EPA+DHA intakes per. Hence, the addition of preformed EPA+DHA seems imperative.

In conclusion, increasing the dietary intake of omega-3 LCPUFA reduces the risk of several diseases, including cardiovascular diseases. Moreover, an improvement of general health might be expected from a reduction of pro-inflammatory markers, reduced serum triglycerides, and/or a reduction in blood pressure. Recommended intakes of EPA+DHA vary from 0.15 to 0.5 En %. To meet the minimum recommended intake of most organizations, the daily intake of EPA+DHA should be at least 500 mg/day (based on a minimum daily food intake of 1500 kcal/day).

The fat fraction according to the invention comprises between 3.0 and 6 weight % of a combination consisting of the ω-3 poly-unsaturated fatty acids alpha-linolenic acid (ALA), docosahexaenoic acid (DHA) and eicosapentaenoic acid (EPA), wherein the amount of ALA >2.5 weight %, more preferably >2.7 weight %, or preferably ranges between 2.5 and 4.0 weight %, and the combined amount of DHA and EPA ≤2.5 weight %, preferably ≤1.0 weight %.

The ω-3 poly-unsaturated fatty acids may be present as triglycerides, ethyl-esters, phospholipids, sphingolipids, glycolipids or other food grade forms.

2. Selection of the Appropriate Fat Sources with a Low LA Content

Almost all current commercial products contain the essential fatty acids linoleic acid (LA) and α-linolenic acid (ALA) to meet the minimum fatty acids requirements. However, these two fatty acids are the precursors for long-chain poly-unsaturated fatty acids (LC PUFA) that are required for normal physiological function of all tissues. The intake of omega-6 by the general population has increased during the last decades of industrialization and the overall consensus is that the Western diet now contains too much omega-6 fatty acids and not enough omega-3 fatty acids (Ailhaud et al. (2006)). This has an effect on a range of physiological and immunological functions.

Recommendations for an minimum intake of LA vary from 1 to 4% of the total caloric intake per day: the French organizations AFSSA and CNERNA-CNRS provided the highest recommendation of 4 En % for adults. None of the national committees and health councils have included a safe upper limit for LA consumption. Nevertheless, the level of LA in the fat composition that is currently used in a number of commercial products is several times higher than the intake that is considered to be adequate in order to prevent a deficiency. Reasons to limit the LA content to an amount close to the highest recommended (adequate) intake of 4 En % are discussed in the following section.

The conversion of the fatty acids LA and ALA into their respective LCPUFAs is controlled by a complex of metabolic factors and the dietary (fatty acid) composition. Among others, increasing the dietary intake of LCPUFAs reduces the conversion of LA and ALA presumably due to product down-regulation of the desaturation and elongation enzymatic pathways that are responsible for the conversion of LA and ALA (Brenna 2002). Moreover, Emken et al. (1994) nicely demonstrated that the conversion of LA as well as ALA into their respective LCPUFAs (ARA, EPA, DHA) was reduced by 40-54%, when the intake of LA was increased from 15 to 30 g/day in volunteers (Emken et al. 1994). These LA intakes corresponded to 4.7 and 9.3 En %, respectively (2800 kcal/day diets), which are in the range of normal dietary intakes and of sip and tube feeds currently on the market. To compensate the reduced endogenous production of long-chain omega-3 fatty acids, EPA and DHA should be supplied via the diet, which is another argument to include fish oil in the composition according to the invention.

High LA intakes not only reduce the conversion of LA and ALA into long-chain fatty acids, but LA also competes with ALA, EPA, as well as DHA for incorporation into tissue phospholipids: the ratio between the dietary omega-6 and omega-3 fatty acids has a strong effect on the eventual tissue composition. As a consequence, high levels of LA have a marked effect on the efficiency of fish oil supplementation. Although intakes of ARA (a downstream product of LA) play a role as well, LA is the predominant PUFA in a normal (western) diet. Hibbeln et al. (2006) compared the worldwide diversity of dietary intakes of omega-6 and omega-3 fatty acids with the risks of cardiovascular and mental illnesses and estimated a tissue target for omega-3 LCPUFAs: 60% omega-3 fatty acids in LCPUFAs (and 40% n-6 fatty acids in LCPUFAs) would be sufficient to protect 98% of the population from cardiovascular mortality. As this level is only reached in populations with extreme consumptions of fish (Japan, Greenland), the proposed a more moderate and realistic tissue target of 50% omega-3 of tissue LCPUFAs (Hibbeln et al. 2006). The 50% omega-3 target for tissue LCPUFAs for instance corresponds to an about 60% reduction of the relative risk for sudden death reported by Albert et al. (2002). By using a formula that takes into account the competition between the fatty acids for incorporation (Lands et al. 1992), the required intake of EPA+DHA was calculated to reach the 50% omega-3 target in relation to the background intake of LA (FIG. 1). This graph illustrates that the effectiveness of fish oil supplementation is enhanced when the LA intake is lowered, or in other words, the effectiveness of fish oil supplementation is strongly reduced when the LA intake is increased. For instance, a more than 3-fold higher EPA+DHA dose is needed to reach the same tissue level at an intake of 8.9 En % LA than at with a diet containing 3.2 En % LA. Knowing that LA competes with EPA and DHA for incorporation into tissues, we can now determine how the LA content of the this invention relates to the recommendations for fish intake, which are in the range of 0.2-0.5 En % EPA+DHA.

In conclusion: to make sure that the level of LA can be regarded as adequate according to all recommendations, a minimum of 4 En % LA is required (French recommendation for adults). As higher levels of LA will reduce the efficiency of fish oil supplementation and detrimentally affect the tissue omega-6/omega-3 ratio, this level of 4 En % should preferably be considered as the maximum level for nutritionally complete products. By modifying the oils currently used in production (see also next section) it is feasible to lower the LA content to 4 En %, though care should be taken to maintain the ALA content above 1 En % ALA (the highest recommended minimum intake of ALA). In this way the omega-6/omega-3 ratio of the formula can be reduced to approximately 3:1. Preferably, the ratio ω-6:ω-3 in the fat composition according to the invention is about 2.5:1-3.5:1, preferably 3:1, wherein the term about means a relative deviation of 10%.

The fat fraction according to the invention comprises between 10 to 15 weight % of linoleic acid (LA).

The linoleic acid may be present as triglycerides, phospholipids, sphingolipids, glycolipids or other food grade forms.

3. Inclusion of Medium-Chain Fatty Acids (MCFAs)

Most of the currently available plant oils contain LA, which makes it difficult to reduce the LA content in a fat composition to the recommended 4 En %. Without compromising the total fat content, a possible solution would be to increase other fatty acids, for example MUFAs (i.e. oleic acid). Unfortunately, available oils that are rich in MUFAs (olive oil, high-oleic sunflower oil) also contain LA, which means that an increase in the MUFA content results in an increase of the LA content as well. Instead, the saturated fatty acid content can be increased: the current saturated fatty acid contents of most of the commercial products are well below the recommended upper intakes. However, increasing the saturated fatty acid content cannot immediately be considered a health benefit, as it for instance increases serum cholesterol levels. One group of saturated fatty acids that can be considered as a healthier alternative are the medium-chain fatty acids (MCFAs) that are naturally found in the form of medium-chain triglycerides (MCTs). MCTs are medium-chain fatty acid esters of glycerol consisting of 3 medium-chain saturated fatty acids (MCFAs) each comprising 6 to 12 carbon atoms.

Natural sources of MCFAs are coconut oils and palm kernel oils. When hydrolyzed, these oils provide concentrated sources of MCFAs with chain lengths of primarily 8 (caprylic or octanoic acid) and 10 (capric or decanoic acid) carbon atoms. Hence, in practice, when MCTs or MCFAs are administered, this is often limited to fatty acids with 8- and 10-carbon chains, although (theoretically) MCFAs also include carbon chains of 6 and 12 carbon atoms.

Hence, the MCFAs according to the invention are preferably selected from MCTs originating from coconut oils and/or palm kernel oils. The chain length of the MCFAs according to the invention is 6, 7, 8, 9, 10, 11 or 12, preferably 8, 9 or 10, most preferably 8 or 10 carbon atoms long, or any mixture thereof.

MCFAs are not considered essential and therefore are not considered a necessary part of the normal diet. Although MCFAs are categorized as saturated fats, they have completely different biochemical and physiological properties compared to long-chain saturated fatty acids, which will be explained below.

(1) The digestion and absorption of MCFAs is easier and faster compared to long-chain fatty acids (LCFAs). MCFAs absorbed from the small intestine (intact or following hydrolysis) are primarily transported via the portal vein to the liver. In contrast, dietary long-chain triglycerides are first hydrolyzed in the small intestine to LCFAs and re-esterified in the mucosal cells of the small intestine to long-chain triglycerides. They are then incorporated into chylomicrons and reach the circulation via the lymphatic system (Bach et al. 1996; Snook et al. 1996). Moreover, the digestion and absorption of MCFAs is not dependent on pancreatic enzymes or bile salts. Particularly patients with malabsorption syndromes and/or pancreatic insufficiency will benefit from a diet rich in MCTs/MCFAs and MCFAs are therefore often used as the preferred fat source for these patients (Marten et al. 2006).

(2) MCFAs readily cross the mitochondrial membrane and are rapidly oxidized (beta-oxidation). This is (in part) due to the fact that fatty acids containing 6 to 12 carbons do not require carnitine to cross the mitochondrial membrane in liver tissue of healthy well-nourished adults, which is in contrast to the carnitine-dependent beta-oxidation of fatty acids with 14 carbon atoms or more (Calabrese et al. 1999). Beta-oxidation of fatty acids results in the production of acetyl-CoA that enters the Kreb's cycle to produce energy, but acetyl-CoA can also be converted into to acetoacetate, beta-hydroxybutyrate, and acetone, collectively called ketone bodies. The rapid uptake of MCFAs into mitochondria can lead to an excess production of acetyl-CoA and a high production of ketone bodies (ketogenic effect), which can be further metabolized in the liver, but may also be transported by the systemic circulation to other tissues to serve as a directly available energy source (Marten et al. 2006).

(3) The preferred β-oxidation of MCFA by mitochondria might protect PUFA from oxidation, which would increase the availability of EPA and DHA for incorporation into tissue phospholipids. A small number of studies have indeed suggested the existence of such an effect. For instance, in one study preterm infants were enterally fed and received either a formula with 40% MCFA (MCT) or one without MCFA for 7 days (Rodriguez et al. 2003). After this period the oxidation of a standard dose of labeled LA was significantly reduced in the MCFA-treated group. Similarly, parenteral administration of an emulsion with MCFA combined with long-chain triglycerides (ratio 1:1) for 8 days resulted in slightly elevated LCPUFA levels in plasma phospholipids and triacylglycerides compared to an emulsion with only PUFAs in another study with preterm infants (Lehner et al. 2006). However, evidence of the protection of PUFAs by providing MCTs/MCFAs in adults is limited.

(4) The preference for β-oxidation of MCFAs by mitochondria for energy production is higher compared to LCFAs, which (theoretically) means less fatty acids are stored in adipose tissue when provided as MCFAs and more is used to generate energy (Metges et al. 1991).

The amount of MCFA or MCT required to reduce the LA content is relatively small: e.g. for a commercial product like Nutrison Standard (NV Nutricia) about 4 En % of MCFAs (C8+C10) is sufficient—together with a modification of other vegetable oil sources—to reduce the LA content from 8.3 to 4 En %. This would correspond to approximately 10 to 15% of the fat composition as MCFA, or 6-8 g MCFA (C8+C10) per day (1500 kcal/day). At these levels, gastrointestinal discomfort is not likely to occur, as much higher levels have been reported to be well tolerated. For instance, a diet with 40 En % fat, of which 50% consisted of MCT, was generally well tolerated, though minor gastrointestinal discomfort and occasional nausea were reported during the first few days of consumption (Bourque et al. 2003). Similarly, a diet with as much as 67% of the fat as MCT (40 En % fat) was reported to be tolerated by volunteers (St-Onge et al. 2003).

In conclusion, to help lower the LA content of the fat composition, the overall PUFA can be lowered by increasing the amount of saturated fat: the total saturated fatty acid content of most of the current commercial products is low (<5 En %) and can be increased within the upper recommended levels (10-12 En %). Although MCFAs are categorised as saturated fat, these fatty acids are easily digestible and are rapidly oxidized to yield energy, in contrast to long-chain fatty acids that are stored in adipose tissue. The inclusion of MCTs/MCFAs can be used as a healthy way of reducing the LA content of the products (within limits). Only small amounts of MCT/MCFA (10-15% of the fat composition) are required to lower the LA content to the desired level of 4 En %, provided that other vegetable oils are modified as well.

The fat fraction according to the invention comprises between 10 to 20 weight % preferably 14 to 18 weight %, most preferably 15.7 to 16.2 weight % of medium-chain fatty acids (MCFA).

The medium-chain fatty acids may be present as triglycerides, phospholipids, sphingolipids, glycolipids or other food grade forms.

4. Inclusion of a Source Rich in Mono-Unsaturated Fatty Acids (MUFAs)

Unsaturated fatty acids are sensitive to oxidation, which leads to the production of damaging oxygen radicals and oxidative damage to surrounding molecules and cells. As the sensitivity for oxidation of fatty acids depends on the number of double bonds in the fatty acid carbon chain, mono-unsaturated fatty acids (MUFAs) are less susceptible to oxidation than polyunsaturated fatty acids.

The development of atherosclerosis, a chronic inflammatory response in the walls of arteries, is triggered by the deposition of lipoproteins (plasma proteins that carry cholesterol and triglycerides) to the arterial wall. Oxidized Low-density lipoprotein (LDL) is believed to be more damaging to the arterial wall than native LDL and oxidation of LDL contributes to the development of atherosclerosis. Elevated concentrations of circulating oxidized LDL show a positive relationship with the severity of acute coronary events and are predictors for CHD both in CHD patients and in the general population (Covas, 2007).

Replacement of saturated fatty acids with oleic acid reduces the risk of developing CHD, among others by incorporation of oleic acid at the expense of linoleic acid (C18:2n-6), which reduces the sensitivity of LDL to oxidation (Reaven et al., 1993; Covas, 2007). Moreover, the total LDL concentration in the blood, as well as factor VII coagulation activity, decrease when foods rich in saturated fat are replaced with foods rich in high-oleic acid sunflower oil in middle-aged men and women within a matter of weeks (Allman-Farinelli et al., 2005).

The mono-unsaturated fatty acid is preferably selected from the group of palmitoleic acid (16:1), oleic acid (18:1), eicosaenoic acid (20:1), erucic acid (22:1), nervoic acid (24:1) or mixtures thereof. Most preferably, the mono-unsaturated fatty acid comprises oleic acid. Most preferably, at least 80 weight % of the mono-unsaturated fatty acid is oleic acid.

The fat fraction according to the invention comprises between 35 to 79 weight %, preferably 50 to 70 weight %, most preferably 50 to 60 weight % of at least one mono-unsaturated fatty acid.

Suitable sources to increase the MUFA content are for example high oleic sunflower oil, high oleic safflower oil, and olive oil.

The mono-unsaturated fatty acids may be present as triglycerides, phospholipids, sphingolipids, glycolipids or other food grade forms.

Preparation of the Fat Fraction

When referred to as the fat fraction according to the invention, the fat composition may be available as a combination or mixture as such, it may be available as a set of components in a defined concentration in a nutritional composition, it may be prepared as such, or it may be prepared by adding the different components LA, ALA, DHA, EPA, MCFA and MUFA, or sources comprising said components together with other ingredients to produce a nutritional composition comprising the fat composition according to the invention. It may also be available as a kit of parts, comprising the separate components LA, ALA, DHA, EPA, MCFA and MUFA, or sources comprising said components to be combined together in the defined amounts, optionally accompanied by instructions how to do so.

The fat composition according to the invention may further comprise a further fatty acid, preferably a fatty acid selected from the group of saturated fatty acids other than MCFA and poly-unsaturated fatty acids other than ALA, DHA and EPA.

The fat composition according to the invention may be manufactured by a skilled person by combining the appropriate fat sources in appropriate amounts. According to one embodiment, the following sources can be combined: Canola oil, high oleic sunflower oil, fish oil and MCT oil. More in particular are combined: about 37 weight % of Canola oil, about 42 weight % of high oleic sunflower oil, about 2 weight % of fish oil and about 17 weight % of MCT oil. It will be obvious to the skilled person that the amounts given above may vary to a certain extent depending on the specific composition of the fat source.

Carbohydrate Fraction

Advantageously, the nutritional composition according to the invention comprises one or more digestible carbohydrates. The digestible carbohydrates positively influence the operational skills of a patient, and add to the advantageous effect of the nutritional composition according to the invention.

According to one embodiment, the liquid nutritional composition according to the invention preferably contains between 1 and 50 gram digestible carbohydrates per 100 ml, more preferably between 5 and 30 grams per 100 ml, more preferably 5, 6, 7, 8, 9, 10, 11, 12, 13, 14, 15, 16, 17, 18, 19, 20, 21, 22, 23, 24, 25, 26, 27, 28, 29, or 30 grams of digestible carbohydrates per 100 ml of a liquid product or any integer and non-integer fraction in between.

According to one embodiment, the liquid nutritional composition according to the invention preferably contains a carbohydrate fraction comprising between 30 and 62 En % of the total energy of the composition.

Examples of digestible carbohydrates are digestible pentoses, digestible hexoses, and digestible oligosaccharides, e.g. digestible disaccharides and digestible trisaccharides. More specifically, one or more digestible carbohydrates may be chosen selected from the group of galactose, mannose, ribose sucrose, trehalose, palatinose, lactose, maltodextrose, maltose and glucose.

Dietary Fibre Fraction

It is commonly known that dietary fibre plays an important role in the nutrition of healthy people. It maintains gut function and clears toxic compounds by providing stool bulk and substrate to intestinal flora, and keeps the gut wall in good condition. Hospital patients who normally receive enteral clinical nutrition need fibre for these purposes, and consumption of the right fibre mixture is especially important for patients who suffer from intestinal problems, such as ulcerative colitis, Crohn's disease, and the like, and who have received antibiotics. Also persons with constipation or with diarrhoea have special interest in this kind of nutrition, and the same applies to persons who are not able to consume the recommended daily amount of fibre for whatever reason (e.g. diet). An optimal fibre composition will:

be similar to the normal fibre composition as consumed by healthy persons in Western countries;
produce beneficial short-chain fatty acids (SCFA) in a balanced ratio and at a sufficient and uniform rate during transit through the ileum and the large intestine;
not produce gas at too high or too low levels;
give sufficient mass to the faeces to facilitate defecation;
not drastically increase the viscosity of the faeces.

A large number of enteral nutritional compositions are known in the prior art comprising optimal and less optimal dietary fibre compositions, such as the ones disclosed in WO 93/100020 A2, EP 0483070 A2, EP 0486425 A2, EP 0504055 A2, EP 0570791 A2, and in particular in EP 0756828 B1.

The enteral nutritional composition according to the invention is intended to comprise any dietary fibre, or any mixture of dietary fibres. In particular, the enteral nutritional composition according to the invention is intended to comprise one or more of fructo-oligosaccharides, inulin, acacia fibre, arabic gum, soy polysaccharide, alpha cellulose and resistant starch.

In a preferred embodiment, the enteral nutritional composition according to the invention comprises a mixture of dietary fibres as disclosed in EP 075 828 B1. More in particular, the liquid enteral nutritional composition comprises 5 to 120 g/l of dietary fibre, wherein the dietary fibre fraction consists of 15 to 50 weight % of soluble non-starch polysaccharides, 15 to 45 weight % of insoluble non-starch polysaccharides, 8 to 70 weight % of non-digestible oligosaccharides comprising at least 8 weight %, on the basis of fibre, of hydrolysed inulin, and comprising resistant starch.

In a preferred embodiment, the enteral nutritional composition according to the invention comprises the dietary fibre mixture as given in Table 6

TABLE 6

Preferred dietary fibre mixture according to the invention

| | |
|---|---|
| 11 weight % Fructo-oligosaccharide (Raftilose) | soluble & highly fermentable |
| 23 weight % Inulin (Raftiline ST) | soluble & highly fermentable |
| 14 weight % Acacia fibre/Arabic gum (non-cellulosic) | completely soluble & highly fermentable |
| 31 weight % Soy polysaccharide (Fibrim) | >about 90% insoluble & fermentable |
| 12 weight % Alpha-cellulose (Vitacel) | insoluble & non-fermentable |
| 9 weight % Resistant starch (Novelose) | insoluble & (about ⅓ fermentable & about ⅔ non-fermentable) |

Micronutrients

The liquid nutritional composition according to the invention may contain minerals, trace elements, vitamins and other micronutrients, and the amounts thereof are in general within the ranges as specified for Food for Special Medical Purposes (FSMP).

More specifically, one or more of the following micronutrients may in particular be present: sodium, kalium, chlorine, calcium, phosphor, manganese, molybdenum, zinc, selenium, magnesium, chromium, iron, copper, fluorine, iodine, vitamin A (retinol), vitamin B1 (thiamine), vitamin B2 (riboflavin), vitamin B3 (niacin), vitamin B5 (pantothenic acid), vitamin B6 (pyridoxine), vitamin B8 (biotin), vitamin B11 (folic acid), vitamin B12 (cyanocobalamin), vitamin C (ascorbic acid), vitamin D2 (ergocalciferol), vitamin D3 (cholecalciferol), vitamin E (alpha-tocopherol), vitamin K, carotenoids, taurine, cysteine, choline, carnitine, and coenzyme Q10.

Viscosity

In one embodiment of the present invention, the viscosity of the liquid enteral nutritional composition is lower than 500 mPa·s, measured at 20° C. (i.e. room temperature) at a shear rate of $100\ s^{-1}$, preferably between 10 and 200 mPa·s, more preferably between 10 and 100 mPa·s, most preferably below 50 mPa·s. The viscosity may suitably be determined using a rotational viscosity meter using a cone/plate geometry. This viscosity is ideal for orally administering the liquid enteral nutritional composition according to the invention because a person may easily consume a serving having a low viscosity such as that displayed by the present invention. This viscosity is also ideal for unit dosages that are tube fed.

In one embodiment of the present invention, the density of the composition ranges between 1.00 g/ml and 1.20 g/ml, especially between 1.05 g/ml and 1.15 g/ml.

Nutritional Composition

Surprisingly, the pea-based protein mixture and fat mixture according to the invention makes it possible to produce a nutritional composition, in particular a liquid enteral nutritional composition with a long shelf life and with a low viscosity, more in particular as a tube feed. Hence, the invention also pertains to a pea-based protein mixture according to the invention for use in the manufacture of a nutritional composition, in particular a liquid nutritional composition, in particular for use as a tube feed, most in particular for long-term tube feeding.

According to a further embodiment, the liquid enteral nutritional composition according to the invention optionally comprises one or more of a carbohydrate fraction, a dietary fibre fraction, and micronutrients Most preferably, such liquid nutritional composition is sterilized or pasteurized.

Dosage Unit

The liquid enteral nutritional composition according to the invention preferably has the form of a complete food, i.e. it can meet all nutritional needs of the user. As such, the liquid enteral nutritional composition according to the invention preferably contains 1000 to 2500 kcal per daily dosage. Depending on the condition of the patient, a daily dose is about 25 to 35 kcal/kg bodyweight/day. Therefore, a typical daily dose for a 70 kg person contains about 2000 kcal. The complete food can be in the form of multiple dosage units, e.g. from 8 (250 ml/unit) to 2 units (1 l/unit) per day for an energy supply of 2000 kcal/day using a liquid enteral nutritional composition according to the invention of 1.0 kcal/ml. Preferably, the nutritional composition is adapted for tube feeding.

The liquid enteral nutritional composition can also be an oral food supplement, for example to be used in addition to a non-medical food or normal diet. Preferably, as an oral supplement, the liquid enteral nutritional composition contains per daily dosage less than 1500 kcal, in particular as a supplement, the liquid enteral nutritional composition contains 500 to 1000 kcal per daily dose. The food supplement can be in the form of multiple dosage units, e.g. from 2 (250 ml/unit) to 10 units (50 ml/unit) per day for an energy supply of 500 kcal/day using a liquid enteral nutritional composition according to the invention of 1.0 kcal/ml.

Preferably, the nutritional composition is packaged, stored and provided in a container such as plastic bag or a pouch or the like. A variety of such containers is known, for example 500 ml, 1000 ml, and 1500 ml containers are known in the art. It should be noted that any suitable container can be used to package, store and provide the nutritional composition according to the invention.

In one embodiment of the present invention, the liquid enteral nutritional composition is provided in a ready to use liquid form and does not require reconstitution or mixing prior to use. The liquid enteral nutritional composition according to the invention can be tube fed or administered orally. For example, the composition according to the invention can be provided in a can, on spike, and hang bag. However, a composition may be provided to a person in need thereof in powder form, suitable for reconstitution using an aqueous solution or water such that the enteral nutritional composition according to the invention is produced. Thus, in one embodiment of the present invention, the present composition may be in the form of a powder, accompanied with instructions to dissolve or reconstitute in an aqueous composition or water to arrive at the liquid nutritional enteral composition according to the present invention. In one embodiment of the present invention, the present liquid nutritional enteral composition may thus be obtained by dissolving or reconstituting a powder, preferably in an aqueous composition, in particular water, more in particular in sterilized water. Such reconstituted liquid composition does not need to be sterilized or pasteurised if used or administered shortly thereafter, but can also be sterilized or pasteurised on the spot before administration.

In one embodiment of the present invention, the composition according to the invention is packaged. The packaging may have any suitable form, for example a block-shaped carton, e.g. to be emptied with a straw; a carton or plastic beaker with removable cover; a small-sized bottle for example for the 80 ml to 200 ml range, and small cups for example for the 10 ml to 30 ml range. Another suitable packaging mode is inclusion of small volumes of liquid (e.g. 10 ml to 20 ml) in edible solid or semi-solid hulls or capsules, for example gelatine-like coverings and the like. Another suitable packaging mode is a powder in a container, e.g. a sachet, preferably with instructions to dissolve or reconstitute in an aqueous composition or water.

Preparation

The liquid nutritional composition according to the invention may be prepared using standard methods known to the skilled person. For example, the liquid nutritional composition, the protein fraction and the fat fraction according to the invention may be prepared as disclosed above ("Preparation of the protein mixture", and "Preparation of the fat mixture"). According to one embodiment, the method for preparing the liquid nutritional composition according to the invention comprises at least the following steps:

(a) mixing the protein, carbohydrate and fibre sources with water to obtain a mixture A (e.g. see: "Preparation of the protein fraction");

(b) mixing said mixture A with a mineral solution comprising minerals and trace elements to obtain a mixture B;

(c) adjusting the pH of said mixture B to at least about 8;

(d) heating said mixture B at a temperature ranging between about 70 to 90° C. for at most about 30 seconds;

(e) adding a fat mixture to said mixture B to obtain a mixture C and homogenising said mixture C (e.g. see: "Preparation of the fat fraction");

(f) mixing said mixture C with a vitamin solution to obtain a mixture D;

(g) adjusting the pH of said mixture D to a value ranging between about 7.8 to 8;

(h) filling said mixture D in a container; and (i) sterilising said container, e.g. in an autoclave.

Effectivity

The present invention also concerns a method of providing nutrition to a person in need thereof, comprising the steps of administering to said person the nutritional composition according to the present invention. Said person may be an elderly person, a person that is in a disease state, a person that is recovering from a disease state, or a person that is malnourished.

The present invention also relates to the use of a liquid nutritional composition according to the invention, as a tube feed, in particular for long-term tube feeding. As used herein, the term "long-term" means greater than one month (30 days). It is obvious that nutrition, when suitable for long-term nutrition, is also suitable for any other shorter period of nutrition, such as medium-term nutrition (10 to 30 days) and short-term nutrition (between 1 and 10 days).

When administered to patients in need of enteral nutrition, a lower incidence of clinical indications was observed for the composition according to the invention, compared to a composition according to the state of the art, in particular for clinical complications of the upper digestive tract (nausea, vomiting, use of antacids), but also for clinical complications of the lower digestive tract (diarrhoea, constipation), gastrointestinal-related adverse events, pneumonia-related adverse events and serious adverse events.

According to one embodiment, the liquid enteral nutritional composition according to the invention may be administered to a patient in need thereof, to prevent said clinical complications of the upper and lower digestive tract.

According to another embodiment, the liquid enteral nutritional composition according to the invention may be administered to a patient in need thereof, who was fed with a prior art enteral nutritional composition and/or has developed said clinical complications of the upper and lower digestive tract, to treat and reduce said clinical complications of the upper and lower digestive tract.

Hence, the present invention also relates to the use of a liquid enteral nutritional composition according to the invention, for the manufacture of a medicament for the prevention and/or treatment of upper and/or lower digestive tract conditions in a tube-fed patient. Preferably, the conditions are selected from the group of nausea and vomiting.

The invention will now be further elucidated by several examples, without being limited thereby.

EXPERIMENTAL

Example 1

Methods: In a two-country, multi-centre, randomised, controlled, double-blind, cross-over designed study, 28 nursing home residents on long term tube feeding received in different order a tube feed comprising the nutritional composition according to the invention (NN) and a control product (Nutrison MF, Nutricia, The Netherlands (N), see Table 7) for 4 weeks (2 weeks each product). Safe use by recording (serious) adverse events ((S)AE), medication use, incidence of diarrhoea and constipation based on stool frequency and consistency (using Bristol Stool Form Scale), and subjective gastro intestinal complaints. Statistical analyses were performed for both the ITT and PP population comparing NN with N. Statistical tests are conducted two-sided with a significance level of 5%. All confidence intervals are presented two-sided with a confidence coefficient of 95%.

TABLE 7

Composition of tested product and control product per 100 ml

| | | Tested Product | Control Product |
|---|---|---|---|
| Energy | kcal | 100 | 100 |
| Protein | En % | 16 | 16 |
| TOTAL | g | 4.0 | 4.0 |
| Casein protein | g | 1.0 | 4.0 |
| Whey protein | g | 1.4 | 0.0 |
| Soy protein | g | 0.8 | 0.0 |
| Pea protein | g | 0.8 | 0.0 |
| Fat | En % | 35 | 35 |
| TOTAL (all fatty acids + glycerol) | g | 3.9 | 3.9 |
| Saturated FA | g | 0.8 | 0.4 |

TABLE 7-continued

Composition of tested product and control product per 100 ml

|  |  | Tested Product | Control Product |
|---|---|---|---|
| of which MCT (C8 + C10) | g | 0.6 | 0.0 |
| Mono-unsaturated FA | g | 2.3 | 2.3 |
| Poly unsaturated FA | g | 0.6 | 1.2 |
| of which: |  |  |  |
| linoleic acid (LA) 18:2 ω-6 | g | 0.42 | 0.9 |
| alpha-linolenic acid (ALA) 18:3 ω-3 | g | 0.10 | 0.2 |
| DHA | g | 0.014 | 0.000 |
| DHA + EPA | g | 0.033 | 0.000 |
| n6:n3 ratio |  | 3.0 | 4.8 |
| Carbohydrates | En % | 49 | 49 |
| TOTAL | g | 12.25 | 12.25 |
| Fibre | En % | 0 | 0 |
| TOTAL | g | 1.5 | 1.5 |
| Minerals* |  |  |  |
| Na | mg | 100 | 100 |
| K | mg | 150 | 150 |
| Cl | mg | 125 | 125 |
| Ca | mg | 80 | 80 |
| P | mg | 72 | 72 |
| Mg | mg | 23 | 23 |
| Trace elements |  |  |  |
| Fe | mg | 1.6 | 1.6 |
| Zn | mg | 1.2 | 1.2 |
| Cu | μg | 180 | 180 |
| Mn | mg | 0.33 | 0.33 |
| F | μg | 100 | 100 |
| Mo | μg | 10 | 10 |
| Se | μg | 5.7 | 5.7 |
| Cr | μg | 6.7 | 6.7 |
| I | μg | 13 | 13 |
| Vitamins |  |  |  |
| vitamin A (retinol) | μg RE | 82 | 82 |
| carotenoids | mg | 0.2 | 0.2 |
| beta-carotene | μg | 86 | — |
| vitamin D3 (cholecalciferol) | μg | 1.0 | 0.7 |
| vitamin E (tocopherol) | mg | 1.3 | 1.3 |
| vitamin K | μg | 5.3 | 5.3 |
| vitamin B1 (thiamine) | mg | 0.15 | 0.15 |
| vitamin B2 (riboflavin) | mg | 0.16 | 0.16 |
| vitamin B3 (niacin) | mg NE | 1.8 | 1.8 |
| vitamin B5 (pantothenic acid) | mg | 0.53 | 0.53 |
| vitamin B6 (pyridoxine) | mg | 0.17 | 0.17 |
| vitamin B8 (biotin) | μg | 4 | 4 |
| vitamin B11 (folic acid) | μg | 27 | 27 |
| vitamin B12 (cyanocobalamin) | μg | 0.21 | 0.21 |
| vitamin C (ascorbic acid) | mg | 10 | 10 |
| Extra additions |  |  |  |
| Choline | mg | 37 | 37 |

Results: Average age and BMI of the ITT population (n=28) was 63 years and 25.5 kg/m². Median (min-max) period of tube-feeding before study was 26 (1-208) months. The mean daily intake during the study was 1339 (786-2100) ml with NN and 1178 (786-2000) ml with N (p=0.043). A definite trend towards lower incidence of constipation was observed in NN (31% vs 50%, p=0.070). The incidences of all other parameters tested were in general lower in NN compared to N (NN vs N: nausea 8% vs 20%, vomiting 4% vs 12%, flatulence 19% vs 16%, diarrhoea 31% vs 36%, constipation 23 vs 36%, use of laxatives 73% vs 79%, anti-diarrhoeals 0% vs 0%, antacids 54% vs 57%, antibiotics 4% vs 18%, opioids 15% vs 18, gastrointestinal AE 12% vs 18%, pneumonia AE 8% vs 14%, other AE 8% vs 14%, SAE 4% vs 14%), although the differences were not significant at a significance level of 0.05. PP (n=21) analyses showed similar trends.

Example 2

Table 8 shows a number of compositions according to the invention, suitable as adult tube feed, paediatric tube feed or adult oral nutritional supplement.

TABLE 8

Enteral compositions according to the invention

| Component | Ex. 1 Adult tube feed | Ex. 2 Paediatric tube feed | Ex. 3 Adult Oral nutritional supplement |
|---|---|---|---|
| Energy value (kcal/100 ml) | 100 | 150 | 240 |
| Protein (En %) | 16 | 16 | 16 |
| Fat (En %) | 35 | 35 | 35 |
| Carbohydrates (En %) | 49 | 49 | 49 |
| Protein (g/100 ml) | 4 | 6 | 9.6 |
| Pea protein | 0.8 | 1.2 | 1.9 |
| Whey protein | 1.4 | 2.1 | 3.4 |
| Casein | 1.0 | 1.5 | 2.4 |
| Soy protein | 0.8 | 1.2 | 1.9 |
| Carbohydrates (g/100 ml) | 12.3 | 18.3 | 29.7 |
| Fat (g/100 ml) | 3.9* | 5.8* | 9.3* |
| Saturated fat | 1.0 | 1.5 | 2.4 |
| MCFA | 0.6 | 0.9 | 1.4 |
| Unsaturated fat | 2.9 | 4.3 | 6.9 |
| MUFA | 2.2 | 3.2 | 5.2 |
| PUFA | 0.7 | 1.1 | 1.7 |
| LA | 0.5 | 0.8 | 1.3 |
| ALA | 0.1 | 0.2 | 0.3 |
| EPA + DHA | 0.03 | 0.03 | 0.03 |
| ALA + EPA + DHA | 0.16 | 0.23 | 0.35 |
| ω-6/ω-3 | 2.9:1 | 3.1:1 | 3.1:1 |
| Viscosity (mPa · s) | 18 | 35 | 70-85 |
| Density (kg/l) | 1.1 | 1.1 | 1.1 |

*in these examples 3.9 g fat equals 3.7 g fatty acids; 5.8 g fat equals 5.5 g fatty acids; 9.3 g fat equals 8.7 g fatty acids.

It should be understood that various changes and modifications to the presently preferred embodiments described herein will be apparent to those skilled in the art. Such changes and modifications may be made without departing from the gist and scope of the invention and without diminishing its advantages. It is therefore intended that such changes and modifications are covered by the appended claims.

REFERENCES

Ailhaud, G., F. Massiera, P. Weill, P. Legrand, J. M. Alessandri and P. Guesnet (2006). "Temporal changes in dietary fats: role of n-6 polyunsaturated fatty acids in excessive adipose tissue development and relationship to obesity." Prog Lipid Res 45(3): 203-36.

Albert, C. M., H. Campos, M. J. Stampfer, P. M. Ridker, J. E. Manson, W. C. Willett and J. Ma (2002). "Blood levels of long-chain n-3 fatty acids and the risk of sudden death." N Engl J Med 346(15): 1113-8.

Allman-Farinelli, M. A., K. Gomes, et al. (2005). "A diet rich in high-oleic-acid sunflower oil favorably alters low-density lipoprotein cholesterol, triglycerides, and factor VII coagulant activity." J Am Diet Assoc 105(7): 1071-9.

Bach, A. C., Y. Ingenbleek and A. Frey (1996). "The usefulness of dietary medium-chain triglycerides in body weight control: fact or fancy?" J Lipid Res 37(4): 708-26.

Bemelmans, W. J., J. Broer, E. J. Feskens, A. J. Smit, F. A. Muskiet, J. D. Lefrandt, V. J. Bom, J. F. May and B. Meyboom-de Jong (2002). "Effect of an increased intake of alpha-linolenic acid and group nutritional education on cardiovascular risk factors: the Mediterranean Alpha-linolenic Enriched Groningen Dietary Intervention (MARGARIN) study." Am J Clin Nutr 75(2): 221-7.
Bourque, C., M. P. St-Onge, A. A. Papamandjaris, J. S. Cohn and P. J. Jones (2003). "Consumption of an oil composed of medium chain triacyglycerols, phytosterols, and N-3 fatty acids improves cardiovascular risk profile in overweight women." Metabolism 52(6): 771-7.
Brenna, J. T. (2002). "Efficiency of conversion of alpha-linolenic acid to long chain n-3 fatty acids in man." Curr Opin Clin Nutr Metab Care 5(2): 127-32.
Burdge, G. C. and S. A. Wootton (2002). "Conversion of alpha-linolenic acid to eicosapentaenoic, docosapentaenoic and docosahexaenoic acids in young women." Br J Nutr 88(4): 411-20.
Calabrese, C., S. Myer, S. Munson, P. Turet and T. C. Birdsall (1999). "A cross-over study of the effect of a single oral feeding of medium chain triglyceride oil vs. canola oil on post-ingestion plasma triglyceride levels in healthy men." Altern Med Rev 4(1): 23-8.
Calder, P. C. (2006). "n-3 polyunsaturated fatty acids, inflammation, and inflammatory diseases." Am J Clin Nutr 83(6 Suppl): 1505S-1519S.
Carnielli, V. P., G. Verlato, F. Pederzini, I. Luijendijk, A. Boerlage, D. Pedrotti and P. J. Sauer (1998). "Intestinal absorption of long-chain polyunsaturated fatty acids in preterm infants fed breast milk or formula." Am J Clin Nutr 67(1): 97-103.
Covas, M. I. (2007). "Olive oil and the cardiovascular system." Pharmacol Res 55(3): 175-86.
Chrysohoou, C., D. B. Panagiotakos, C. Pitsavos, J. Skoumas, X. Krinos, Y. Chloptsios, V. Nikolaou and C. Stefanadis (2007). "Long-term fish consumption is associated with protection against arrhythmia in healthy persons in a Mediterranean region—the ATTICA study." Am J Clin Nutr 85(5): 1385-91.
Davidson, M. H., K. C. Maki, J. Kalkowski, E. J. Schaefer, S. A. Torri and K. B. Drennan (1997). "Effects of docosahexaenoic acid on serum lipoproteins in patients with combined hyperlipidemia: a randomized, double-blind, placebo-controlled trial." J Am Coll Nutr 16(3): 236-43.
Deutsche Gesellschaft für Ernährung e. V. (2006). Evidenzbasierte Leitlinie: Fettkon-sum and Prävention ausgewählter ernährungsmitbedingter Krankheiten. Bonn.
Emken, E. A., R. O. Adlof and R. M. Gulley (1994). "Dietary linoleic acid influences desaturation and acylation of deuterium-labeled linoleic and linolenic acids in young adult males." Biochim Biophys Acta 1213(3): 277-88.
Gerster, H. (1998). "Can adults adequately convert alpha-linolenic acid (18:3n-3) to eicosapentaenoic acid (20:5n-3) and docosahexaenoic acid (22:6n-3)?" Int J Vitam Nutr Res 68(3): 159-73.
Goyens, P. L., M. E. Spilker, P. L. Zock, M. B. Katan and R. P. Mensink (2006). "Conversion of alpha-linolenic acid in humans is influenced by the absolute amounts of alpha-linolenic acid and linoleic acid in the diet and not by their ratio." Am J Clin Nutr 84(1): 44-53.
Hansen, J. B., J. O. Olsen, L. Wilsgard, V. Lyngmo and B. Svensson (1993). "Comparative effects of prolonged intake of highly purified fish oils as ethyl ester or triglyceride on lipids, haemostasis and platelet function in normolipaemic men." Eur J Clin Nutr 47(7): 497-507.
Health Council of the Netherlands (2006). Guidelines for a healthy diet 2006. publication nr. 2006/21. The Hague.
Hibbeln, J. R., L. R. Nieminen, T. L. Blasbalg, J. A. Riggs and W. E. Lands (2006). "Healthy intakes of n-3 and n-6 fatty acids: estimations considering worldwide diversity." Am J Clin Nutr 83(6 Suppl): 1483S-1493S.
ISSFAL (2004). Recommendations for intake of polyunsaturated fatty acids in healthy humans. Brighton, International Society for the Study of Fatty Acids and Lipids.
Lands, W. E., B. Libelt, A. Morris, N. C. Kramer, T. E. Prewitt, P. Bowen, D. Schmeisser, M. H. Davidson and J. H. Burns (1992). "Maintenance of lower proportions of (n-6) eicosanoid precursors in phospholipids of human plasma in response to added dietary (n-3) fatty acids." Biochim Biophys Acta 1180(2): 147-62.
Lehner, F., H. Demmelmair, W. Roschinger, T. Decsi, M. Szasz, K. Adamovich, R. Arnecke and B. Koletzko (2006). "Metabolic effects of intravenous LCT or MCT/LCT lipid emulsions in preterm infants." J Lipid Res 47(2): 404-11.
Luley, C., H. Wieland and J. Grünwald (1990). "Bioavailability of omega-3 fatty acids: ethyl ester preparations are as suitable as triglyceride preparations." Akt.Ernähr.-Med. 15: 123-5.
Marten, B., M. Pfeuffer and J. Schrezenmeier (2006). "Medium-chain triglycerides." International Dairy Journal 16: 1374-82.
Metges, C. C. and G. Wolfram (1991). "Medium- and long-chain triglycerides labeled with 13C: a comparison of oxidation after oral or parenteral administration in humans." J Nutr 121(1): 31-6.
Mozaffarian, D., A. Geelen, I. A. Brouwer, J. M. Geleijnse, P. L. Zock and M. B. Katan (2005). "Effect of fish oil on heart rate in humans: a meta-analysis of randomized controlled trials." Circulation 112(13): 1945-52.
Reaven, P., S. Parthasarathy, et al. (1993). "Effects of oleate-rich and linoleate-rich diets on the susceptibility of low density lipoprotein to oxidative modification in mildly hyper-cholesterolemic subjects." J Clin Invest 91(2): 668-76.
Rodriguez, M., S. Funke, M. Fink, H. Demmelmair, M. Turini, G. Crozier and B. Koletzko (2003). "Plasma fatty acids and [13C]linoleic acid metabolism in pre-term infants fed a formula with medium-chain triglycerides." J Lipid Res 44(1): 41-8.
Sala-Vila, A., C. Campoy, A. I. Castellote, F. J. Garrido, M. Rivero, M. Rodríguez-Palmero and M. C. López-Sabater (2006). "Influence of dietary source of docosahexaenoic and arachidonic acids on their incorporation into membrane phospholipids of red blood cells in term infants." Prostaglandins Leukot Essent Fatty Acids 74(2): 143-8.
Sala-Vila, A., A. I. Castellote, C. Campoy, M. Rivero, M. Rodriguez-Palmero and M. C. Lopez-Sabater (2004). "The source of long-chain PUFA in formula supplements does not affect the fatty acid composition of plasma lipids in full-term infants." J Nutr 134(4): 868-73.
Schwellenbach, L. J., K. L. Olson, K. J. McConnell, R. S. Stolcpart, J. D. Nash and J. A. Merenich (2006). "The triglyceride-lowering effects of a modest dose of docosahexaenoic acid alone versus in combination with low dose eicosapentaenoic acid in patients with coronary artery disease and elevated triglycerides." J Am Coll Nutr 25(6): 480-5.
Serhan, C. N. (2006). "Novel chemical mediators in the resolution of inflammation: resolvins and protectins." Anesthesiol Clin 24(2): 341-64.
Sijben, J. W. and P. C. Calder (2007). "Differential immunomodulation with long-chain n-3 PUFA in health and chronic disease." Proc Nutr Soc 66(2): 237-59.
Snook, J. T., S. Park, G. Wardlaw, R. Jandacek, D. Palmquist, M.-S. Lee and J. Hoover (1996). "Chylomicron fatty acid composition and serum lipid concentrations in subjects fed caprenin or palm oil/palm kernel oil as the major dietary fat." Nutrition Research 16(6): 925-36.

St-Onge, M. P., C. Bourque, P. J. Jones, R. Ross and W. E. Parsons (2003a). "Medium-versus long-chain triglycerides for 27 days increases fat oxidation and energy expenditure without resulting in changes in body composition in overweight women." Int J Obes Relat Metab Disord 27(1): 95-102.

Tapiero, H., G. N. Ba, P. Couvreur and K. D. Tew (2002). "Polyunsaturated fatty acids (PUFA) and eicosanoids in human health and pathologies." Biomed Pharmaco-ther 56(5): 215-22.

Theobald, H. E., A. H. Goodall, N. Sattar, D. C. Talbot, P. J. Chowienczyk and T. A. Sanders (2007). "Low-dose docosahexaenoic acid lowers diastolic blood pressure in middle-aged men and women." J Nutr 137(4): 973-8.

Williams, C. M. and G. Burdge (2006). "Long-chain n-3 PUFA: plant v. marine sources." Proc Nutr Soc 65(1): 42-50.

Zampelas, A., D. B. Panagiotakos, C. Pitsavos, U. N. Das, C. Chrysohoou, Y. Skoumas and C. Stefanadis (2005). "Fish consumption among healthy adults is associated with decreased levels of inflammatory markers related to cardiovascular disease: the ATTICA study." J Am Coll Cardiol 46(1): 120-4.

The invention claimed is:

1. A liquid enteral nutritional composition comprising:
   (i) a protein fraction comprising 30 to 50 weight % of intact vegetable protein comprising at least 15 to 25 weight % pea protein, the protein fraction further comprising a dairy protein selected from the group of casein, micellar casein, caseinate, and whey protein;
   (ii) a fat fraction comprising:
      (a) 8 to 15 weight % of linoleic acid (LA);
      (b) 3.0 to 6.0 weight % of a combination consisting of the ω-3 poly-unsaturated fatty acids alpha-linolenic acid (ALA), docosahexaenoic acid (DHA) and eicosapentaenoic acid (EPA), wherein the amount of ALA is greater than 2.5 weight % and the combined amount of DHA and EPA is less than or equal to 2.5 weight %;
      (c) 10 to 20 weight % of medium-chain fatty acid (MCFA); and
      (d) 35 to 79 weight % of mono-unsaturated fatty acid (MUFA),
   wherein all relative amounts are calculated based on the total amount of fatty acids in the fat fraction.

2. The liquid enteral nutritional composition according to claim 1, further comprising one or more of a carbohydrate fraction, a dietary fibre fraction, and micronutrients.

3. The liquid enteral nutritional composition according to claim 1, wherein the protein fraction further comprises a vegetable protein other than pea protein selected from the group consisting of soy, rice, and wheat protein.

4. The liquid enteral nutritional composition according to claim 1, wherein the protein fraction comprises 50 - 70 wt % of dairy proteins, relative to the total protein in the protein fraction.

5. The liquid enteral nutritional composition according to claim 1, wherein the protein fraction comprises pea, soy, casein and whey protein.

6. The liquid enteral nutritional composition according to claim 1, wherein the protein fraction has the following amino acid profile in gram per 100 gram total protein in the protein fraction:
   (a) Cysteine : at least 1.1 g/100 g;
   (b) Phenylalanine : at least 4.0 g/100 g; and
   (c) Tyrosine : at least 3.7 g/ 100 g.

7. The liquid enteral nutritional composition according to claim 1, wherein the fat fraction comprises 4.0 to 5.0 weight % of a combination consisting of the ω-3 poly-unsaturated fatty acids ALA, DHA and EPA, calculated relative to the total amount of fatty acids in the fat fraction.

8. The liquid enteral nutritional composition according to claim 1, wherein the combined amount of DHA and EPA is less than or equal to 1.0 weight %, calculated relative to the total amount of fatty acids in the fat fraction.

9. The liquid enteral nutritional composition according to claim 1, wherein the fat fraction comprises:
   (a) 12.5 to 14.5 weight % of LA;
   (b) 4.0 to 5.0 weight % of a combination consisting of the ω-3 poly-unsaturated fatty acids ALA, DHA, and EPA, wherein the amount of ALA ranges between 2.5 and 4.0 weight % and the combined amount of DHA and EPA is less than or equal to 1.0 weight %;
   (c) 14 to 18 weight % of medium-chain fatty acid (MCFA); and
   (d) 40 to 70 weight % of mono-unsaturated fatty acid (MUFA),
   wherein all relative amounts are calculated based on the total amount of fatty acids in the fat fraction.

10. The liquid enteral nutritional composition according to claim 1, further comprising one or more of fructo-oligosaccharides, inulin, acacia fibre, arabic gum, soy polysaccharide, alpha cellulose and resistant starch.

11. The liquid enteral nutritional composition according to claim 1, wherein the fat fraction comprises 12.5 to 14.5 weight %, of LA, calculated relative to the total amount of fatty acids in the fat fraction.

12. A liquid nutritional composition comprising:
   a protein mixture comprising more than 25 and up to 80 weight % of intact vegetable protein comprising pea protein and a protein selected from the group consisting of soy, rice, and wheat protein;
   (ii) a fat fraction comprising:
      (a) 8 to 15 weight % of linoleic acid (LA);
      (b) 3.0 to 6.0 weight % of a combination consisting of the ω-3 poly-unsaturated fatty acids alpha-linolenic acid (ALA), docosahexaenoic acid (DHA) and eicosapentaenoic acid (EPA), wherein the amount of ALA is greater than 2.5 weight % and the combined amount of DHA and EPA is less than or equal to 2.5 weight %;
      (c) 10 to 20 weight % of medium-chain fatty acid (MCFA); and
      (d) 35 to 79 weight % of mono-unsaturated fatty acid (MUFA),
   wherein all relative amounts are calculated based on the total amount of fatty acids in the fat fraction.

* * * * *